United States Patent
Nakase et al.

(10) Patent No.: US 11,117,937 B2
(45) Date of Patent: Sep. 14, 2021

(54) METHOD FOR PRODUCING FIBROIN-LIKE PROTEIN

(71) Applicants: AJINOMOTO CO., INC., Tokyo (JP); SPIBER INC., Yamagata (JP)

(72) Inventors: Kentaro Nakase, Kanagawa (JP); Yoshinori Takashima, Kanagawa (JP); Takeshi Nagahiko, Kanagawa (JP)

(73) Assignees: AJINOMOTO CO., INC., Tokyo (JP); SPIBER INC., Yamagata (JP)

( * ) Notice: Subject to any disclaimer, the term of this patent is extended or adjusted under 35 U.S.C. 154(b) by 601 days.

(21) Appl. No.: 15/989,400

(22) Filed: May 25, 2018

(65) Prior Publication Data

US 2018/0265555 A1   Sep. 20, 2018

Related U.S. Application Data

(63) Continuation of application No. PCT/JP2016/084760, filed on Nov. 24, 2016.

(30) Foreign Application Priority Data

Nov. 25, 2015   (JP) .............................. JP2015-229987

(51) Int. Cl.
| | |
|---|---|
| *C12N 15/09* | (2006.01) |
| *C12N 15/71* | (2006.01) |
| *D01F 4/02* | (2006.01) |
| *C07K 14/435* | (2006.01) |
| *C12P 21/02* | (2006.01) |

(52) U.S. Cl.
CPC ........ *C07K 14/43518* (2013.01); *C12N 15/71* (2013.01); *C12P 21/02* (2013.01); *C07K 2319/02* (2013.01); *C07K 2319/034* (2013.01); *C07K 2319/035* (2013.01); *C12N 15/09* (2013.01); *D01F 4/02* (2013.01)

(58) Field of Classification Search
None
See application file for complete search history.

(56) References Cited

U.S. PATENT DOCUMENTS

| 5,919,662 | A | 7/1999 | Haze et al. | |
|---|---|---|---|---|
| 9,926,348 | B2 * | 3/2018 | Nakase | ............ C07K 14/43518 |
| 10,752,660 | B2 * | 8/2020 | Nakase | ................. C12N 15/70 |
| 2007/0214520 | A1 | 9/2007 | Scheibel et al. | |
| 2014/0058066 | A1 | 2/2014 | Sekiyama et al. | |
| 2017/0066805 | A1 | 3/2017 | Nakase et al. | |
| 2020/0291078 | A1 * | 9/2020 | Joshi | ...................... C07K 14/78 |

FOREIGN PATENT DOCUMENTS

| EP | 3147368 A1 | 3/2017 |
|---|---|---|
| JP | 02-502065 A | 7/1990 |
| JP | 2013-085531 A | 5/2013 |
| JP | 2013-188141 A | 9/2013 |
| WO | WO2006/008163 A2 | 1/2006 |
| WO | WO2012/165476 A1 | 12/2012 |

OTHER PUBLICATIONS

Yang, G., et al., "Biosynthesis and characterization of a non-repetitive polypeptide derived from silk fibroin heavy chain," Materials Science and Engineering C 2016;59:278-285.
Zabelina, V., et al., "Genome engineering and parthenocloning in the silkworm, *Bombyx mori*," J. Biosci. 2015;40(3):645-655.
Salazar-Cavazos, E., et al., "Optimal Performance of the Tryptophan Operon of *E. coli*: A stochastic, Dynamical, Mathematical-Modeling Approach," Bull. Math. Biol. 2014;76:314-334.
Kim, M.-D., et al., "Two-Step Fed-Batch Culture of Recombinant *Escherichia coli* for Production of Bacillus licheniformis Maltogenic Amylase," J. Microbiol. Biotechnol. 2002;12(2):273-278.
Supplementary European Search Report for European Patent App. No. 16868608.7 (dated Mar. 8, 2019).
International Search Report and Written Opinion for PCT Patent App. No. PCT/JP2016/084760 (dated Jan. 10, 2017) with English translation of the ISR.
Shimizu, N., et al., "Fed-Batch Cultures of Recombinant *Escherichia coli* with Inhibitory Substance Concentration Monitoring," J. Ferment. Technol. 1988;66(2):187-191.
Jensen, E. B., et al., "Production of Recombinant Human Growth Hormone in *Escherichia coli*: Expression of Different Precursors and Physiological Effects of Glucose, Acetate, and Salts," Biotechnol. Bioeng. 1990;36:1-11.
Han, K., et al., "Acetic Acid Formation in *Escherichia coli* Fermentation," Biotechnol. Bioeng. 1992;39:663-671.
Shiloach, J., et al., "Effect of Glucose Supply Strategy on Acetate Accumulation, Growth, and Recombinant Protein Production by *Escherichia coli* BL21 (λDE3) and *Escherichia coli* JM109," Biotechnol. Bioeng. 1996;49:421-428.
International Preliminary Report on Patentability for PCT Patent App. No. PCT/JP2016/084760 (dated Jun. 7, 2018).

* cited by examiner

*Primary Examiner* — Channing S Mahatan

(74) *Attorney, Agent, or Firm* — Cermak Nakajima & McGowan LLP; Shelly Guest Cermak

(57) ABSTRACT

A method for producing a fibroin-like protein is provided. A fibroin-like protein is produced by a method of culturing *Escherichia coli* having a gene encoding the fibroin-like protein in a medium, inducing expression of the gene encoding the fibroin-like protein, and collecting the fibroin-like protein, wherein accumulation of an organic acid at the time of inducing the expression is reduced, and wherein the gene is expressed under control of a tryptophan promoter.

15 Claims, 7 Drawing Sheets

Specification includes a Sequence Listing.

(A) Addition of IAA solution before start of culture (B) Addition of IAA solution at 5th hour of culture (A) Addition of IAA solution before start of culture (B) Addition of IAA solution at 5th hour of culture

METHOD FOR PRODUCING FIBROIN-LIKE PROTEIN

This application is a Continuation of, and claims priority under 35 U.S.C. § 120 to, International Application No. PCT/JP2016/084760, filed Nov. 24, 2016, and claims priority therethrough under 35 U.S.C. § 119 to Japanese Patent Application No. 2015-229987, filed Nov. 25, 2015, the entireties of which are incorporated by reference herein. Also, the Sequence Listing filed electronically herewith is hereby incorporated by reference (File name: 2018-05-25T_US-581 Seq List; File size: 45 KB; Date recorded: May 25, 2018).

BACKGROUND OF THE INVENTION

Field of the Invention

The present invention relates to a method for producing a fibroin-like protein based on heterogeneous expression using *Escherichia coli*.

Brief Description of the Related Art

Fibroin is a fibrous protein that is found in spider's thread and silkworm's thread. Spider's thread is a material that is four times stronger than steel, and tougher than carbon fiber and aramid fiber, and is highly elastic and resistant to heat. Therefore, the ability to produce the constituents that make up these threads, such as fibroin or a fibrous protein having a structure similar to that of fibroin (henceforth generically referred to as "fibroin-like protein") on a large-scale is of great interest.

As for the production of fibroin-like protein, heterogeneous expression thereof using *Escherichia coli* has been reported (see WO2012/165476 and WO2006/0081632).

It is known that, in heterogeneous expression of a protein using *Escherichia coli*, the accumulation of acetic acid in the medium correlates with reduction of cell growth and reduction of the expression amount of protein (see Bech Jensen, E. and Carlsen, S., Biotechnol. Bioeng., 36:1-11, 1990; and Shimizu, N., Fukuzono, S., Fujimori, K., Nishimura, N. and Odawara, Y. J., Ferment. Technol., Vol. 66, No. 2, 187-191, 1988). Namely, when human growth hormone (hGH) is heterogeneously expressed in *Escherichia coli* by continuous culture (chemostat) in which acetic acid concentration was controlled at a certain constant level, specific production rate of hGH reduced by about 38% when acetic acid concentration is maintained at 2.4 g/L; and if acetic acid concentration exceeded 6.1 g/L, cell growth is also reduced (Bech Jensen, E. and Carlsen, S., Biotechnol. Bioeng., 36:1-11, 1990). These inhibition effects became more marked under a low pH condition in which the acid is present in a non-dissociated state (Bech Jensen, E. and Carlsen, S., Biotechnol. Bioeng., 36:1-11, 1990). When β-galactosidase is heterogeneously expressed in *Escherichia coli*, cell growth and β-galactosidase accumulation are increased by controlling the acetic acid concentration in the medium to be 33 mM or lower in fed-batch culture in which feeding was intermittently stopped when accumulation of acetic acid is confirmed in the medium (Shimizu, N., Fukuzono, S., Fujimori, K., Nishimura, N. and Odawara, Y. J., Ferment. Technol., Vol. 66, No. 2, 187-191, 1988). However, none of these references refer or suggest the influence of acetic acid concentration at the time of inducing the expression of a protein.

It is also known that, when *Escherichia coli* is cultured, acetic acid accumulation can be reduced by reducing glucose uptake rate (Han K., Lim H. C., and Hong J., Biotechnol. Bioeng., March 15; 39(6):663-71, 1992).

The tryptophan promoter (trp promoter) is an inducible promoter. It has been known that gene expression from the trp promoter can be induced by, for example, depletion of tryptophan (Trp) or addition of 3-beta-indoleacrylic acid (IAA).

SUMMARY OF THE INVENTION

An aspect of the present invention is to provide an efficient method for producing a fibroin-like protein. It has been found that when a fibroin-like protein is heterogeneously expressed under control of a tryptophan promoter (trp promoter) in *Escherichia coli*, production of the fibroin-like protein can be improved by reducing the accumulation of organic acid when expression of the fibroin-like protein is induced It is an aspect of the present invention to provide a method for producing a fibroin-like protein, the method comprising: (A) culturing *Escherichia coli* having a gene encoding the fibroin-like protein in a medium; (B) inducing expression of the gene encoding the fibroin-like protein; and (C) collecting the fibroin-like protein, wherein accumulation of an organic acid at the time of said inducing the expression is reduced, and wherein the gene is expressed under the control of a tryptophan promoter.

It is a further aspect of the present invention to provide the method as described above, wherein said inducing occurs by depleting tryptophan in the medium, adding 3-beta-indoleacrylic acid to the medium, or a combination thereof.

It is a further aspect of the present invention to provide the method as described above, wherein said inducing occurs either by depleting tryptophan in the medium; or by depleting tryptophan in the medium and adding 3-beta-indoleacrylic acid to the medium.

It is a further aspect of the present invention to provide the method as described above, wherein the concentration of tryptophan in the medium is lower than 50 mg/L during said depleting.

It is a further aspect of the present invention to provide the method as described above, wherein the step (A) comprises a culture period A1 and a culture period A2, wherein the culture period A2 occurs after the culture period A1, wherein the concentration of tryptophan in the medium during the culture period A1 is 50 mg/L or higher, and wherein the concentration tryptophan in the medium during the culture period A2 is lower than 50 mg/L.

It is a further aspect of the present invention to provide the method as described above, wherein said inducing expression occurs at the timepoint of switching from the culture period A1 to the culture period A2.

It is a further aspect of the present invention to provide the method as described above, wherein at the beginning of said culturing, the medium contains tryptophan at a concentration of 50 mg/L or higher.

It is a further aspect of the present invention to provide the method as described above, wherein at the beginning of said culturing, the medium contains 3-beta-indoleacrylic acid.

It is a further aspect of the present invention to provide the method as described above, wherein the method comprises adding 3-beta-indoleacrylic acid to the medium after the beginning of said culturing.

It is a further aspect of the present invention to provide the method as described above, wherein the amount of organic acid that has accumulated in the medium at the time of said inducing the expression is 3.3 g/L or lower.

It is a further aspect of the present invention to provide the method as described above, wherein OD620 at the time of said inducing the expression is 50 or more.

It is a further aspect of the present invention to provide the method as described above, wherein said accumulation of the organic acid is reduced by limiting the amount of a carbon source during a period before said inducing the expression.

It is a further aspect of the present invention to provide the method as described above, wherein the carbon source in the medium is limited to 1.0 g/L or lower during the period before said inducing the expression.

It is a further aspect of the present invention to provide the method as described above, wherein the carbon source is glucose.

It is a further aspect of the present invention to provide the method as described above, wherein the accumulation of the organic acid is reduced by modifying the *Escherichia coli* so that an ability to produce the organic acid is reduced.

It is a further aspect of the present invention to provide the method as described above, wherein the *Escherichia coli* is auxotrophic for tryptophan.

DETAILED DESCRIPTION OF THE EXEMPLARY EMBODIMENTS

<1> Fibroin-Like Protein

Figure 1A:
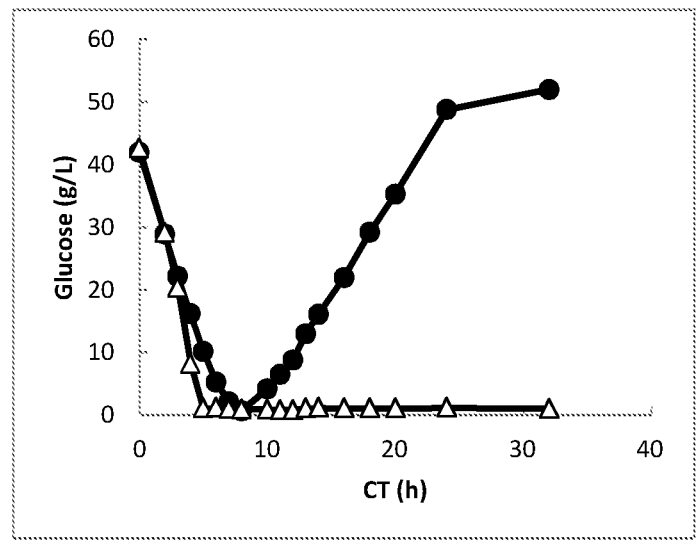
FIGS. 1A and 1B show graphs showing the change of the glucose concentration over time when adding IAA solution before the start of culture (1A) and after 5 hours of culture (1B). The symbols • indicate the results obtained with the control condition, and the symbols Δ indicate the results obtained with the saccharide-limited condition.

The term "fibroin-like protein" is a generic term referring to fibroin and a fibrous protein having a structure similar to that of fibroin.

The term "fibroin" refers to a fibrous protein that makes up spider's thread or silkworm's thread. That is, examples of fibroin include fibroin of spider, and fibroin of silkworm. Species of spider, species of silkworm, and type of thread are not particularly limited. Examples of spider species can include *Araneus diadematus* and *Nephila clavipes*. Other examples of spider species can include *Araneus bicentenarius*, *Argiope amoena*, *Argiope aurantia*, *Argiope trifasciata*, *Cyrtophora moluccensis*, *Dolomedes tenebrosus*, *Euprosthenops australis*, *Gasteracantha mammosa*, *Latrodectus geometricus*, *Latrodectus hesperus*, *Macrothele holsti*, *Nephila pilipes*, *Nephila madagascariensis*, *Nephila senegalensis*, *Octonoba varians*, *Psechrus sinensis*, *Tetragnatha kauaiensis*, and *Tetragnatha versicolor*. Examples of spider fibroin can include proteins of drag line, frame thread, and radius thread produced by major ampullate gland (major ampullate gland proteins), proteins of scaffolding thread produced by minor ampullate gland (minor ampullate gland proteins), and proteins of spiral line produced by flagelliform gland (flagelliform gland proteins). Specific examples of spider fibroin can include, for example, the major ampullate gland proteins ADF3 and ADF4 of *Araneus diadematus* and the major ampullate gland proteins MaSp1 and MaSp2 of *Nephila clavipes*. Examples of silkworm can include *Bombyx mori* and *Samia cynthia*. The amino acid sequences of these fibroins and the nucleotide sequences of the genes encoding these fibroins (also referred to as "fibroin gene") can be obtained from public databases such as NCBI (ncbi.nlm.nih.gov). The amino acid sequence of ADF3 of *Araneus diadematus* (partial; NCBI AAC47010.1 GI: 1263287) is shown as SEQ ID NO: 3.

The phrase "fibrous protein having a structure similar to that of fibroin" can refer to a fibrous protein having a sequence similar to a repetitive sequence of fibroin. The "sequence similar to a repetitive sequence of fibroin" may be a sequence actually found in fibroin, or may be a sequence similar to such a sequence. Examples of the fibrous protein having a structure similar to that of fibroin can include polypeptides derived from the large spigot drag line proteins described in WO2012/165476 and recombinant spider silk proteins described in WO2006/008163. Examples of the fibrous protein having a structure similar to that of fibroin also can include the fibroin-like protein used in the Examples section and the ADF3 protein used in WO2015/178465. The nucleotide sequence of the fibroin-like protein gene used in the Examples section is shown in SEQ ID NO: 1, and the amino acid sequence of the fibroin-like protein encoded by the gene is shown in SEQ ID NO: 2. The nucleotide sequence of the ADF3 gene used in WO2015/

178465 is shown in SEQ ID NO: 4, and the amino acid sequence of the ADF3 protein encoded by the gene is shown in SEQ ID NO: 5. Incidentally, the nucleotide sequence of positions 12-1994 of SEQ ID NO: 4 encodes the amino acid sequence shown in SEQ ID NO: 5.

Namely, examples of the "sequence similar to a repetitive sequence of fibroin" can include a sequence represented by the following formula I (WO2012/165476, henceforth also referred to as "repetitive sequence I"):

REP1-REP2... (I)

In the formula I, REP1 is an amino acid sequence having a continuous sequence of one or more of the amino acids alanine and glycine. When REP1 contains both alanine and glycine, the order of alanine and glycine is not particularly limited. For example, in REP1, alanine may be present for two or more residues, glycine may be present for two or more residues, or alanine and glycine may alternate in a line. The length of REP1 may be, for example, 2 residues or longer, 3 residues or longer, 4 residues or longer, or 5 residues or longer, or may be 20 residues or shorter, 16 residues or shorter, 13 residues or shorter, 12 residues or shorter, or 8 residues or shorter, or may be within a range defined by any combination of these ranges. The length of REP1 may be, for example, 2 to 20 residues, 3 to 16 residues, 4 to 13 residues, 4 to 12 residues, or 5 to 8 residues. REP1 corresponds to, for example, the crystalline region of the fibroin of spider that forms the crystalline β sheet within the fiber.

In the formula I, REP2 is an amino acid sequence having one or more of the amino acids glycine, serine, glutamine, and alanine. In REP2, the total number of glycine, serine, glutamine, and alanine residues may be, for example, 40% or more, 60% or more, or 70% or more of the total number of amino acid residues of REP2. The length of REP2 may be, for example, 2 residues or longer, 10 residues or longer, or 20 residues or longer, or may be 200 residues or shorter, 150 residues or shorter, 100 residues or shorter, or 75 residues or shorter, or may be within a range defined by any combination of these ranges. The length of REP2 may be, for example, 2 to 200 residues, 10 to 150 residues, 20 to 100 residues, or 20 to 75 residues. REP2 corresponds to, for example, an amorphous region of the fibroin of spider showing flexibility, most part of which lacks regular structure.

The repetition number of the repetitive sequence I is not particularly limited. The repetition number of the repetitive sequence I may be, for example, 2 or more, 5 or more, or 10 or more, or may be 100 or less, 50 or less, or 30 or less, and it may be within a range defined by any combination of these ranges. The configurations of REP1 and REP2 of the respective repetitive sequences may be or may not be the same.

The fibrous protein having a structure similar to that of fibroin may have, for example, an amino acid sequence showing a homology of 90% or higher to an amino acid sequence around the C-terminus of the fibroin of spider at the C-terminus, in addition to the sequence similar to the repetitive sequence of fibroin. Examples of the amino acid sequence around the C-terminus of the fibroin of spider can include, for example, the amino acid sequence of the C-terminus 50 residues of the fibroin of spider, the amino acid sequence of the C-terminus 50 residues of the same of which the C-terminus 20 residues are removed, and the amino acid sequence of the C-terminus 50 residues of the same of which the C-terminus 29 residues are removed. Specific examples of the amino acid sequence around the C-terminus of the fibroin of spider can include, for example, the sequence of the positions 587 to 636 (C- terminus 50 residues), the sequence of the positions 587 to 616, and the sequence of the positions 587 to 607 of ADF3 of *Araneus diadematus* (partial; NCBI AAC47010.1 GI: 1263287) shown as SEQ ID NO: 3.

Specific examples of the fibrous protein having a sequence similar to the repetitive sequence of fibroin, and having an amino acid sequence showing a homology of 90% or higher to an amino acid sequence around the C-terminus of the fibroin of spider at the C-terminus include, for example, the fibroin-like protein used in the Examples section (SEQ ID NO: 2).

That is, the fibroin-like protein may be, for example, a protein having any of the amino acid sequences of fibroin-like proteins disclosed in the aforementioned database or documents, or a protein having the amino acid sequence of SEQ ID NO: 2 or 5. The fibroin-like protein may also be, for example, a protein having a partial sequence of any of those amino acid sequences. Examples of the partial sequence of an amino acid sequence can include a portion having a sequence similar to the repetitive sequence of fibroin. Specific examples of the partial sequence of an amino acid sequence can include, for example, the amino acid sequence of positions 25-610 of SEQ ID NO: 5 and the amino acid sequence of positions 53-536 of SEQ ID NO: 5. Similarly, a gene encoding a fibroin-like protein (also referred to as "fibroin-like protein gene") may be, for example, a gene having any of the nucleotide sequences of the fibroin genes disclosed in the aforementioned database or documents, or a gene having the nucleotide sequence of SEQ ID NO: 1 or the nucleotide sequence of positions 12-1994 of SEQ ID NO: 4. The fibroin-like protein gene may also be, for example, a gene having a partial sequence of any of those nucleotide sequences. Examples of the partial sequence of a nucleotide sequence can include a portion encoding an amino acid sequence having and/or including a sequence similar to the repetitive sequence of fibroin.

The fibroin-like protein may be a variant of any of the fibroin-like proteins exemplified above, that is, the fibroin and the fibrous proteins having a structure similar to that of fibroin exemplified above, so long as the original function thereof is maintained. Similarly, the fibroin-like protein gene may be a variant of any of the fibroin-like protein genes exemplified above, that is, the genes encoding fibroin and the fibrous proteins having a structure similar to that of fibroin exemplified above, so long as the original function thereof is maintained. Such variants that maintain the original function can also be referred to as "conservative variants". Examples of the conservative variants can include, for example, homologues and artificially-modified proteins or genes of the fibroin-like proteins exemplified above and genes encoding them.

The expression "the original function is maintained" can mean that a variant of a gene or protein has a function, such as an activity and/or property, corresponding to the function of the original gene or protein. That is, for the fibroin-like protein, the expression "the original function is maintained" can mean that a variant of the protein is the fibrous protein. In the case of the fibroin-like protein gene, the expression "the original function is maintained" can mean that a variant of the gene encodes a protein that maintains the original function, namely, the fibrous protein. The term "fibrous protein" can refer to a protein that has a fibrous form under predetermined conditions. That is, the fibrous protein may be a protein expressed in a fibrous form, or a protein that is not in a fibrous form when it is expressed, but can be processed into a fibrous form. The fibrous protein may be, for example, a protein that is expressed as an inclusion body, and can be then processed into a fibrous form by an appropriate technique. Examples of methods for processing a protein into a fibrous form can include the method disclosed in WO2012/165476.

Examples of homologue of the fibroin-like protein can include, for example, a protein obtained from a public database by BLAST search or FASTA search using any of the aforementioned amino acid sequences of fibroin-like proteins as a query sequence. A homologue of the aforementioned fibroin-like protein genes can be obtained by, for example, PCR using a chromosome of various microorganisms as the template, and oligonucleotides prepared on the basis of any of the aforementioned nucleotide sequences of fibroin-like protein genes as the primers.

Conservative variants of the fibroin-like protein and fibroin-like protein gene are described herein.

The fibroin-like protein may be a protein having any of the aforementioned amino acid sequences of fibroin-like proteins including substitution, deletion, insertion, and/or addition of one or several amino acid residues at one or several positions, so long as the original function of the protein is maintained. Although the number meant by the term "one or several" can differ depending on the positions of amino acid residues in the three-dimensional structure of the protein, or the types of amino acid residues, it can be specifically, for example, 1 to 50, 1 to 40, 1 to 30, 1 to 20, 1 to 10, 1 to 5, or 1 to 3.

The aforementioned substitution, deletion, insertion, and/or addition of one or several amino acid residues are/is each a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, and/or the like of amino acid residues as mentioned above includes a naturally occurring mutation due to an individual difference, or a difference of species of the organism from which the gene is derived (mutant or variant).

The fibroin-like protein may be a protein having an amino acid sequence showing a homology of 80% or higher, 90% or higher, 95% or higher, 97% or higher, 99% or higher, to any of the aforementioned amino acid sequences of fibroin-like proteins, so long as the original function is maintained. "Homology" can also mean "identity".

The fibroin-like protein may be a protein encoded by a DNA that is able to hybridize under stringent conditions with a probe that can be prepared from any of the aforementioned nucleotide sequences of fibroin-like protein genes, such as a sequence complementary to the whole sequence or a partial sequence of any of the aforementioned nucleotide sequences, so long as the original function is maintained. Such a probe can be prepared by PCR using oligonucleotides prepared on the basis of any of the aforementioned nucleotide sequences as the primers, and a DNA fragment containing any of the aforementioned nucleotide sequences as the template. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization can be, for example, 50° C., 2×SSC, and 0.1% SDS.

Furthermore, arbitrary codons in the fibroin-like protein gene may have been replaced with respective equivalent codons. That is, the fibroin-like protein gene may be a variant of any of the fibroin-like protein genes exemplified above due to the degeneracy of the genetic code. For example, the fibroin-like protein gene may be a gene modified so that it has optimal codons according to codon frequencies in a chosen host.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, such as an alignment, for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The fibroin-like protein may be a fusion protein with another peptide. The "another peptide" is not particularly limited so long as a fibroin-like protein having desired property can be obtained. The "another peptide" can be appropriately selected as required depending on various conditions such as purpose of use thereof. Examples of the "another peptide" can include a peptide tag, and recognition sequence for a protease. The "another peptide" may be bound to, for example, the N-terminus or C-terminus, or the both of the fibroin-like protein. As the "another peptide", one kind of peptide may be used, or two or more kinds of peptides may be used in combination.

Specific examples of the peptide tag can include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. The peptide tag can be used for, for example, detection and purification of the expressed fibroin-like protein.

Specific examples of the recognition sequence for a protease can include the recognition sequence for the HRV3C protease, the recognition sequence for the factor Xa protease, and the recognition sequence for the proTEV protease. The recognition sequence for a protease can be used for, for example, cleavage of the expressed fibroin-like protein. Specifically, for example, when the fibroin-like protein is expressed as a fusion protein with a peptide tag, if a recognition sequence for a protease is introduced into a linking part between the fibroin-like protein and the peptide tag, the peptide tag can be removed from the expressed fibroin-like protein by using the protease to obtain the fibroin-like protein not having the peptide tag.

Specific examples of such a fusion protein can include ADF3 of *Araneus diadematus* to which a His tag and the HRV3C protease recognition sequence have been added at the N-terminus (SEQ ID NO: 5).

The fibroin-like protein gene may be one having any of the nucleotide sequences of fibroin-like protein genes exemplified above and conservative variants thereof, in which arbitrary codons are replaced with equivalent codons. For example, the fibroin-like protein gene may be modified so that it has codons optimized for codon usage observed in the chosen host.

<2> Bacterium

The bacterium can be an *Escherichia coli* having a gene encoding a fibroin-like protein (fibroin-like protein gene).

The bacterium can have a fibroin-like protein gene, and therefore can have an ability to produce a fibroin-like protein (fibroin-like protein-producing ability). The expression "the bacterium can have a fibroin-like protein-producing ability" can mean that, for example, when the bacterium is cultured in a medium, it produces and accumulates a fibroin-like protein in the medium and/or cells thereof to such an extent that the fibroin-like protein can be collected from the medium and/or cells.

*Escherichia coli* is not particularly limited, and examples thereof can include bacteria classified as *Escherichia coli* according to the taxonomy known to those skilled in the field of microbiology. Specific examples of *Escherichia coli* can include, for example, *Escherichia coli* K-12 strains such as the W3110 strain (ATCC 27325) and MG1655 strain (ATCC 47076); *Escherichia coli* K5 strain (ATCC 23506); *Escherichia coli* B strains such as the BL21(DE3) strain and recA⁻ strains thereof such as the BLR(DE3) and Rosetta(DE3) strains; and derivative strains of these.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org/). The registration numbers of the strains are listed in the catalogue of the American Type Culture Collection. The BL21(DE3) strain is available from, for example, Life Technologies (product number C6000-03). The BLR(DE3) strain is available from, for example, Merck Millipore (product number 69053). The Rosetta(DE3) strain is available from, for example, Novagen.

The bacterium may be an auxotrophic strain. Such an auxotrophic strain may have one kind of auxotrophy, or may have two or more kinds of auxotrophies. Examples of the auxotrophy can include amino acid auxotrophy such as isoleucine auxotrophy and tryptophan auxotrophy, and nucleic acid auxotrophy. For example, the *Escherichia coli* BLR(DE3) strain shows isoleucine auxotrophy (Schmidt M., Romer L., Strehle M., Scheibel T., Biotechnol. Lett., 2007, 29 (11):1741-1744). In addition, for example, tryptophan auxotrophy can be imparted to *Escherichia coli* by disrupting, such as by deleting, one or more genes selected from tryptophan biosynthesis genes such as trpEDCBA. Specifically, for example, tryptophan auxotrophy can be imparted to *Escherichia coli* by deleting the entire trpEDCBA operon.

Furthermore, the bacterium may be a bacterium in which the recA gene has been disrupted (e.g. deleted).

An *Escherichia coli* strain having a fibroin-like protein gene can be obtained by introducing the gene into any of such *Escherichia coli* strains as mentioned above. *Escherichia coli* strains to which a fibroin-like protein gene is to be or has been introduced can also be generically referred to as "host".

A fibroin-like protein gene can be obtained by cloning from an organism having the fibroin-like protein gene. For the cloning, a nucleic acid such as genomic DNA or cDNA containing the gene can be used. A fibroin-like protein gene can also be obtained by chemical synthesis (Gene, 60(1), 115-127 (1987)).

By appropriately modifying the obtained fibroin-like protein gene, a variant thereof can also be obtained. The gene can be modified by a known technique. For example, an objective mutation can be introduced into a target site of DNA by the site-specific mutation method. That is, for example, a coding region of a gene can be modified by the site-specific mutagenesis method so that a specific site of the encoded protein can include substitution, deletion, insertion, or addition of amino acid residues. Examples of the site-specific mutagenesis method can include a method of using PCR (Higuchi, R., 61, in PCR Technology, Erlich, H. A. Eds., Stockton Press (1989); Carter P., Meth., in Enzymol., 154, 382 (1987)), and a method of using a phage (Kramer, W and Frits, H. J., Meth. in Enzymol., 154, 350 (1987); Kunkel, T. A. et al., Meth. in Enzymol., 154, 367 (1987)).

The method for introducing a fibroin-like protein gene into a host is not particularly limited. In the host, a fibroin-like protein gene may be present in such a manner that it can be expressed under control of a tryptophan promoter (trp promoter). In the host, a fibroin-like protein gene may be present on a vector autonomously replicable out of the chromosome such as plasmid, cosmid, or phagemid, or may be introduced into the chromosome. The host may have only one copy of a fibroin-like protein gene, or may have two or more copies of a fibroin-like protein gene. The host may have only one kind of fibroin-like protein gene, or may have two or more kinds of fibroin-like protein genes.

The expression "a fibroin-like protein gene is expressed under control of a trp promoter" is not limited to when the fibroin-like protein gene is expressed directly from the trp promoter, called direct expression, but also can include when the expression of the fibroin-like protein gene is indirectly induced via the expression of another gene, such as a gene other than the fibroin-like protein gene, from the trp promoter, also called indirect expression. Direct expression, for example, can include when the fibroin-like protein gene is ligated downstream of the trp promoter and the expression of the gene from the trp promoter is induced, and the gene thereby can be expressed directly from the trp promoter. Indirect expression, for example, can include when the expression of the fibroin-like protein gene from another promoter, such as a promoter other than the trp promoter, can be indirectly induced via a product, such as transcription or translation product, of another gene expressed directly from the trp promoter. For example, the transcription of a gene from a T3 promoter, T5 promoter, T7 promoter, and SP6 promoter can be performed by a T3 RNA polymerase, T5 RNA polymerase, T7 RNA polymerase, and SP6 RNA polymerase, respectively. Hence, for example, when the fibroin-like protein gene is ligated downstream of the T3 promoter, T5 promoter, T7 promoter, or SP6 promoter and the corresponding RNA polymerase is inducibly expressed from the trp promoter, the expression of the fibroin-like protein gene thereby can be indirectly induced.

Examples of the trp promoter can include a promoter of a tryptophan operon. Examples of the tryptophan operon can include a trpEDCBA operon native to *Escherichia* bacteria such as *Escherichia coli*. The nucleotide sequence of the trp promoter of the *Escherichia coli* K-12 MG1655 strain is shown as SEQ ID NO: 6. That is, the trp promoter may be, for example, a promoter having any of the nucleotide sequences of the trp promoters exemplified above, for example, the nucleotide sequence of SEQ ID NO: 6. The trp promoter may be, for example, a conservative variant of any of the trp promoters exemplified above, for example a conservative variant of the promoter having the nucleotide sequence of SEQ ID NO: 6. That is, for example, each of the trp promoters exemplified above can be used as it is, or after being modified as required. The term "trp promoter" can include not only the trp promoters exemplified above, but also can include conservative variants thereof. The aforementioned descriptions concerning conservative variants of the fibroin-like protein can be applied mutatis mutandis to conservative variants of the trp promoter. For example, the trp promoter may be a DNA having a nucleotide sequence showing a homology of 80% or higher, 90% or higher, 95% or higher, 97% or higher, 99% or higher, to the nucleotide sequence of SEQ ID NO: 6, so long as the original function is maintained. The term "original function" used for the trp promoter can refer to a function of inducibly expressing a gene ligated immediately downstream of the trp promoter in response to depletion of tryptophan (Trp) in a medium, presence of 3-beta-indoleacrylic acid (IAA) in a medium, or a combination thereof. The function of the trp promoter can be confirmed by confirming induced expression of a gene due to depletion of Trp in a medium, supply of IAA to a medium, or a combination thereof. The induced expression of a gene can be confirmed by, for example, using a reporter gene. Similarly, when using the trp promoter in combination with another promoter such as the T3 promoter, such another promoter can also be used as it is, or after being modified as required.

A terminator for termination of gene transcription may be located downstream of a gene. The terminator is not particularly limited so long as it functions in the bacterium as described herein. The terminator may be a terminator derived from the host, or a heterogenous terminator. The terminator may be the native terminator of the fibroin-like protein gene, or a terminator of another gene. Specific examples of the terminator can include, for example, T7 terminator, T4 terminator, fd phage terminator, tet terminator, and trpA terminator.

A fibroin-like protein gene can be introduced into a host by, for example, using a vector containing the gene. A vector containing a fibroin-like protein gene can also be referred to a recombinant DNA of a fibroin-like protein gene. The recombinant DNA of a fibroin-like protein gene can be constructed by, for example, ligating a DNA fragment containing the fibroin-like protein gene with a vector that functions in a host. By transforming the host with the recombinant DNA of a fibroin-like protein gene, a transformant into which the recombinant DNA has been introduced is obtained, namely, the gene can be introduced into the host. As the vector, a vector autonomously replicable in the host cell can be used. The vector can be a multi-copy vector. Furthermore, the vector can have a marker such as an antibiotic resistance gene for selection of transformant. The vector may also contain a promoter and a terminator. The vector may be, for example, a vector derived from a bacterial plasmid, vector derived from a yeast plasmid, vector derived from a bacteriophage, cosmid, phagemid, or the like. Specific examples of vector autonomously replicable in *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (TaKaRa), pACYC series vectors, and broad host spectrum vector RSF1010. When such a recombinant DNA is constructed, for example, a coding region of a fibroin-like protein ligated downstream of a promoter, such as the trp promoter, may be incorporated into a vector, or a coding region of a fibroin-like protein may be incorporated into a vector downstream of a promoter, such as the trp promoter, originally contained in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

A fibroin-like protein gene can also be introduced into, for example, a chromosome of a host. A gene can be introduced into a chromosome, for example, by using homologous recombination (Miller, J. H., Experiments in Molecular Genetics, 1972, Cold Spring Harbor Laboratory). Examples of gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy of the gene may be introduced, or two or more copies of the gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Homologous recombination may also be performed by using an appropriate sequence on a chromosome such as a gene unnecessary for carrying out the present invention as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a coding region of a fibroin-like protein ligated downstream of a promoter, such as the trp promoter, may be incorporated into a chromosome, or a coding region of a fibroin-like protein may be incorporated into a chromosome downstream from a promoter, such as the trp promoter, originally present on the chromosome.

Introduction of a gene into a chromosome can be confirmed by, for example, Southern hybridization using a probe having a sequence complementary to the entire gene or a part thereof, or PCR using primers prepared on the basis of the nucleotide sequence of the gene.

When two or more of genes are introduced, it is sufficient that the genes each are expressibly harbored by the bacterium. For example, all the genes may be present on a single expression vector or a chromosome. Furthermore, the genes may be separately present on two or more expression vectors, or separately present on a single or two or more expression vectors and a chromosome. In addition, so long as the concept of an induced expression of the fibroin-like protein gene under control of the trp promoter is attained, an operon made up of two or more genes may also be introduced. The phrase "introducing two or more genes" can include, for example, introducing two or more kinds of fibroin-like protein genes, introducing a fibroin-like protein gene in combination with a gene encoding an RNA polymerase for indirectly inducing the expression of the fibroin-like protein gene, introducing a fibroin-like protein gene in combination with a trp repressor gene, and combinations thereof.

The method for the transformation is not particularly limited, and conventionally known methods can be used. Examples of the transformation method can include, for example, treating recipient cells with calcium chloride so as to increase permeability thereof for DNA, which has been reported for the *Escherichia coli* K-12 strain (Mandel, M. and Higa, A., J. Mol. Biol., 1970, 53, 159-162), preparing competent cells from cells which are in the growth phase, followed by introducing DNA, which has been reported for *Bacillus subtilis* (Duncan, C. H., Wilson, G. A. and Young, F. E., 1977, Gene, 1:153-167), and so forth. Alternatively, a method of making DNA-recipient cells into protoplasts or spheroplasts, which can easily take up recombinant DNA, and then introducing a recombinant DNA into the DNA-recipient cells can also be used to transform cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G R., 1978, Proc. Natl. Acad. Sci. USA, 75:1929-1933). Furthermore, as the transformation method, the electric pulse method reported for coryneform bacteria (Japanese Patent Laid-open (Kokai) No. 2-207791) can also be used.

Expression of a gene from the trp promoter can be induced by releasing the suppression of the expression which occurs when expression is not being actively induced. This suppression of the expression occurs by a tryptophan repressor (trp repressor). Specifically, it has been reported that the trp repressor binds to tryptophan to become activated, and then binds to an operator site in the trp promoter, which results in repression of the expression of a gene from the trp promoter. Hence, the bacterium as described herein can have a gene encoding the trp repressor (trp repressor gene). The expression "having a trp repressor gene" can also be expressed as "having a trp repressor". The bacterium can inherently have the trp repressor gene, or can be modified so as to have the trp repressor gene. Furthermore, an appropriate trp repressor gene can be introduced into the bacterium, instead of, or in addition to, the presence of an inherent trp repressor gene present in the bacterium. The trp repressor gene to be introduced is not particularly limited, so long as it attains an induced expression of a gene from the trp promoter.

Examples of the trp repressor can include a TrpR protein, which is encoded by a trpR gene. Examples of the trpR gene can include the trpR gene native to *Escherichia* bacteria such as *Escherichia coli*. The nucleotide sequence of the trpR gene of the *Escherichia coli* K-12 MG1655 strain is shown as SEQ ID NO: 8, and the amino acid sequence of the TrpR protein encoded by the gene is shown in SEQ ID NO: 9. That is, the trp repressor gene may be, for example, a gene having any of the nucleotide sequences of the trp repressor genes exemplified above, for example, the nucleotide sequence of SEQ ID NO: 8. Also, the trp repressor may be, for example, a protein having any of the amino acid sequences of the trp repressors exemplified above, for example, the amino acid sequence of SEQ ID NO: 9. The trp repressor gene may be, for example, a conservative variant of any of the trp repressor genes exemplified above, for example, a conservative variant of the gene having the nucleotide sequence of SEQ ID NO: 8. Also, the trp repressor may be, for example, a conservative variant of any of the trp repressors exemplified above, for example, a conservative variant of the protein having the amino acid sequence of SEQ ID NO: 9. The term "trpR gene" can include not only the trpR genes exemplified above, but also can include conservative variants thereof. Also, the term "TrpR protein" can include not only the TrpR proteins exemplified above, but also can include conservative variants thereof. The aforementioned descriptions concerning conservative variants of the fibroin-like protein gene and fibroin-like protein can be applied mutatis mutandis to conservative variants of the trp repressor gene and trp repressor. The term "original function" used for the trp repressor can refer to a function of participating in an induced expression of a gene from the trp promoter as described above, and specifically, may refer to a function of repressing the expression of a gene from the trp promoter under conditions where requirements for induction of the expression from the trp promoter are not satisfied. Examples of the "conditions where requirements for induction of the expression from the trp promoter are not satisfied" can include conditions when Trp in a medium is not depleted and conditions where IAA is not contained in a medium. The function of the trp repressor can be confirmed by confirming an induced expression of a gene from the trp promoter due to depletion of Trp in a medium, supply of IAA to a medium, or a combination thereof. The induced expression of a gene can be confirmed by, for example, using a reporter gene.

Introduction of the trp repressor gene can be carried out, for example, in the same manner as that of introduction of the fibroin-like protein gene described above. The promoter for expressing the trp repressor gene is not particularly limited, so long as it functions in the host and induced expression of the fibroin-like protein gene under control of the trp promoter is attained. The promoter for expressing the trp repressor gene may be an inducible one, or may be a constitutive one. In particular a constitutive promoter, for example, may be used, from the viewpoint of cost. The promoter for expressing the trp repressor gene may be a promoter derived from the host, or a heterogenous promoter. The promoter for expressing the trp repressor gene may be the native promoter of the trp repressor gene, or a promoter of another gene. Typically, the promoter for expressing the trp repressor gene may be a promoter other than the trp promoter. Examples of promoters that function in *Escherichia coli* can include bla promoter, lac promoter, trc promoter, tac promoter, araBAD promoter, tetA promoter, rhaP$_{BAD}$ promoter, proU promoter, cspA promoter, $\lambda P_L$ promoter, $\lambda P_R$ promoter, phoA promoter, pstS promoter, T3 promoter, T5 promoter, T7 promoter, and SP6 promoter.

The bacterium may further be modified so that an ability to produce an organic acid (organic acid-producing ability) is reduced. When two or more kinds of modifications are introduced to the bacterium, the order of introduction of them is not particularly limited. That is, for example, *Escherichia coli* that has been introduced with a fibroin-like protein gene may be further modified so that the organic acid-producing ability is reduced, or a fibroin-like protein gene may be introduced into *Escherichia coli* that has been modified so that the organic acid-producing ability is reduced.

The expression "an organic acid-producing ability is reduced" can mean that, for example, when the bacterium is cultured under a typical culture condition under which an organic acid is by-produced, the amount of the organic acid accumulated in the medium is smaller than that observed when a control strain is cultured under the same condition, and may also mean that the organic acid is not accumulated in the medium at all. Examples of the "typical culture condition under which an organic acid is by-produced" can include conditions that the feeding rate of a carbon source into the culture system is higher than the consumption rate of the carbon source by the bacterium in the culture system, that is, in other words, conditions that the culture is performed in the presence of a sufficient amount of the carbon source. When the culture is performed in the presence of a sufficient amount of carbon source, the concentration of the carbon source in the culture system is maintained to be high. Therefore, the expression "culture is performed in the presence of a sufficient amount of carbon source" may mean that the culture is performed so that the concentration of the carbon source in the medium is not lower than a certain concentration. The culture may be performed as batch culture, fed-batch culture, continuous culture, or a combination of these. Examples of the "conditions that the culture is performed in the presence of a sufficient amount of carbon source" can include, for example, conditions that the culture is performed so that the glucose concentration in the medium is always not lower than a certain concentration from the start of the culture to immediately before inducing the expression. The term "immediately before inducing the expression" may refer to, for example, any time point within a period of from 1 hour before inducing the expression to the induction of the expression. The term "not lower than a certain concentration" may refer to, for example, a concentration of 0.5 g/L or higher, 1.0 g/L or higher, 2.0 g/L or higher, 3.0 g/L or higher, 5.0 g/L or higher, or 10.0 g/L or higher. Specific examples of the "typical culture condition under which an organic acid is by-produced" can include, for example, conditions including when the culture is aerobically performed as batch culture by using a liquid medium containing a sufficient amount of glucose, such as the control conditions described in the Examples herein. Examples of the control strain can include non-modified strains such as wild-type strain and parental strain. Examples of the organic acid can include, for example, acetic acid, citric acid, succinic acid, formic acid, and pyruvic acid. In the bacterium, an ability to produce one kind of organic acid may be reduced, or an ability to produce two or more kinds of organic acids may be reduced, and at least the ability to produce acetic acid, among these organic acids, can be reduced.

A modification for reducing an organic acid-producing ability can be attained by, for example, a mutagenesis treatment. That is, a non-modified strain such as wild-type strain and parental strain can be subjected to a mutagenesis treatment, and a strain showing a reduced organic acid-producing ability can be selected. Examples of the mutagenesis treatment can include irradiation of X-ray, irradiation of ultraviolet, and treatment with a mutagenesis agent such as N-methyl-N'-nitro-N-nitrosoguanidine (MNNG), ethyl methanesulfonate (EMS), and methyl methanesulfonate (MMS).

Modification for reducing an organic acid-producing ability can be attained by, for example, reducing the activity of an enzyme that is a part of the biosynthetic pathway of an organic acid, specifically, by reducing the activity of an enzyme of a biosynthetic pathway of an organic acid as compared with a non-modified strain. For example, examples of enzymes of acetic acid biosynthesis pathway can include acetate kinase, phosphotransacetylase, pyruvate-formate lyase, pyruvate oxidase, and acetyl Co-A synthetase. The amino acid sequences of these enzymes of various *Escherichia coli* strains and the nucleotide sequences of the genes encoding these enzymes can be obtained from, for example, public databases such as NCBI (ncbi.nlm.nih.gov). In the bacterium, the activity or activities of one kind or two or more kinds of enzymes of biosynthesis pathways of organic acids may be reduced.

Also, for example, by enhancing the phosphoenolpyruvate carboxylase activity, specifically, by enhancing the phosphoenolpyruvate carboxylase activity as compared with a non-modified strain, the acetic acid-producing ability can be reduced. The phosphoenolpyruvate carboxylase activity can be enhanced by, for example, increasing the expression of a gene encoding phosphoenolpyruvate carboxylase. Examples of the method for enhancing the expression of a gene can include increasing the copy number of the gene, and increasing the transcription or translation of the gene. The copy number of a gene can be increased by introducing the gene into a chromosome of host. The copy number of a gene can also be increased by introducing a vector containing the gene into the host. Introduction of a gene can be carried out, for example, in the same manner as that of introduction of the fibroin-like protein gene and trp repressor gene described above. The transcription or translation of a gene can be increased by modifying an expression control sequence such as promoter, Shine-Dalgarno (SD) sequence (also referred to as ribosome binding site (RBS)), and spacer region between RBS and start codon.

Hereinafter, the methods for reducing the activity of a protein such as various enzymes will be described.

The expression "the activity of a protein is reduced" can mean that the activity of the protein is reduced as compared with a non-modified strain. Specifically, the expression "the activity of a protein is reduced" may mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. Specific examples of the non-modified strain also can include strains exemplified above in relation to the description of *Escherichia coli*. In an embodiment, the activity of a protein may be reduced as compared with the *E. coli* K-12 MG1655 strain. The phrase "the activity of a protein is reduced" can also include when the activity of the protein has completely disappeared. More specifically, the expression "the activity of a protein is reduced" may mean that the number of protein molecules per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The phrase "the number of molecules of the protein per cell is reduced" also can mean when the protein does not exist at all. The phrase "the function of each molecule of the protein is reduced" also can include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene is reduced as compared with a non-modified strain. Specifically, the expression "the expression of a gene is reduced" may mean that the expression of the gene per cell is reduced as compared with that of a non-modified strain such as a wild-type strain and parent strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The phrase "the expression of a gene is reduced" also can include when the gene is not expressed at all. The phrase "the expression of a gene is reduced" can also mean that "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence can be modified. Furthermore, a part of or the entire expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described herein.

The modification for reducing the activity of a protein can also be attained by, for example, disrupting a gene encoding the protein. The expression "a gene is disrupted" can mean that a gene is modified so that a protein that can normally function is not produced. The phrase "a protein that normally functions is not produced" can include when the protein is not produced at all from the gene, and when the protein of which the function (such as activity or property) per molecule is reduced or eliminated is produced from the gene.

Disruption of a gene can be attained by, for example, deleting a part of or the entire coding region of the gene on a chromosome. Furthermore, the entire gene, including sequences upstream and downstream from the gene on a chromosome, may be deleted. The region to be deleted may be any region, such as an N-terminus region, an internal region, or a C-terminus region, so long as the activity of the protein can be reduced. Deletion of a longer region can usually more surely inactivate the gene. Furthermore, the reading frames of the sequences upstream and downstream from the region to be deleted may not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. The reading frames of the sequences upstream and downstream from the insertion site may not be the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a deficient-type gene modified so that it is unable to produce a protein that normally functions, and transforming a host with a recombinant DNA containing the deficient-type gene to cause homologous recombination between the deficient-type gene and the wild-type gene on a chromosome and thereby substitute the deficient-type gene for the wild-type gene on the chromosome. In this procedure, if a marker gene selected according to the characteristics of the host such as auxotrophy is included in the recombinant DNA, the operation becomes easier. Examples of the deficient-type gene can include a gene including deletion of all or a part of the gene, gene including a missense mutation, gene including a nonsense mutation, gene including a frame shift mutation, and gene introduced with an insertion sequence such as a transposon or marker gene. The protein encoded by the deficient-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex having a plurality of subunits, a part or all of the subunits may be modified, so long as the activity of the protein is eventually reduced. That is, for example, a part or all of the genes that encode the respective subunits may be disrupted or the like. Furthermore, when there is a plurality of isozymes of a protein, a part or all of the activities of the isozymes may be reduced, so long as the activity of the protein is eventually reduced. That is, for example, a part or all of the genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

<3> Method of the Present Invention

The method as described herein is a method for producing a fibroin-like protein by (A) culturing *Escherichia coli* having a gene encoding the fibroin-like protein in a medium, (B) inducing expression of the gene encoding the fibroin-like protein, and (C) collecting the fibroin-like protein, wherein accumulation of an organic acid at the time of inducing the expression as mentioned above is reduced, and wherein the gene is expressed under control of a trp promoter. The steps (A), (B), and (C) can also be referred to as "cultivation step", "expression induction step", and "collection step", respectively.

That is, first, the culture of the bacterium is started. Expression of the fibroin-like protein gene is induced at an appropriate time after the start of the culture. After the induction of the expression, the culture is further continued so that the bacterium produces and accumulates a fibroin-like protein in the medium and/or cells of the bacterium. The phrase "time of inducing the expression" can refer to the time when expression is induced, namely, when inducing the expression of the fibroin-like protein gene. The period from the start of the culture to when expression is induced can also be referred to as "period before inducing the expression", and the period from when expression is induced to the end of the culture can also be referred to as "period after inducing the expression".

By inducing expression, the expression amount of the fibroin-like protein gene is increased as compared with that observed under a normal condition. By the induction of the expression, the expression amount of the fibroin-like protein gene may be increased to at least 2 times or more, 3 times or more, 4 times or more, of that observed under a normal condition. The expression "the expression amount of the fibroin-like protein gene is increased as compared with that observed under a normal condition" can also include when the fibroin-like protein gene not expressed under a normal condition at all is expressed. The term "normal condition" can refer to a condition where the fibroin-like protein gene is expressed under the control of a non-inducible promoter, or a condition where requirements for induction of the expression from the trp promoter are not satisfied. Examples of the "condition where the fibroin-like protein gene is expressed under control of a non-inducible promoter" can include conditions where the fibroin-like protein gene is expressed under control of a native non-inducible promoter of the gene. Examples of the "condition where requirements for induction of the expression from the trp promoter are not satisfied" can include conditions where Trp in a medium is not depleted and conditions where IAA is not contained in a medium.

Culture conditions are not particularly limited, so long as the bacterium can proliferate during the period before inducing the expression, accumulation of an organic acid at the time of inducing the expression is reduced, and a fibroin-like protein is produced and accumulated during the period after inducing the expression. During the period after inducing the expression, the bacterium may proliferate, or may not proliferate. The culture conditions for the period before inducing the expression and the period after inducing the expression may be the same, or may not be the same. The culture conditions can be appropriately selected by those skilled in the art according to various conditions such as type of the method for reducing accumulation of an organic acid.

The length of "the period before inducing the expression", that is, the timing for inducing the expression, can be appropriately chosen according to various conditions such as culture conditions. The induction of the expression may be performed, for example, at a time point on or after 0 hour, 1 hour, 2 hours, or 3 hours after the start of the culture, at a time point on or before 240 hours, 200 hours, 160 hours, 120 hours, or 80 hours after the start of the culture, or at a time point within a period defined by any combination of these earliest and latest time points. The induction of the expression may also be performed, for example, when OD620 (Optical Density at 620 nm) of the culture broth becomes within a certain range. OD620 at the time of inducing the expression, for example, may be 50 or more, 100 or more, 150 or more, 180 or more, or 200 or more, may be 500 or less, 400 or less, 300 or less, or 200 or less, or may be within a range defined by any a combination of these ranges. The length of "the period after inducing the expression" can be appropriately chosen according to various conditions such as culture conditions. Culture period after inducing the expression, for example, may be 1 hour or longer, 4 hours or longer, or 8 hours or longer, may be 240 hours or shorter, 200 hours or shorter, 160 hours or shorter, 120 hours or shorter, or 80 hours or shorter, or may be within a range defined by any combination of these ranges.

Methods for inducing the expression are not particularly limited, so long as the expression of the fibroin-like protein gene under control of the trp promoter is induced. Expression can be induced by, for example, depletion of tryptophan (Trp) in the medium, addition of 3-beta-indoleacrylic acid (IAA) to the medium, or a combination thereof. The expression may be induced at least by depletion of Trp in the medium, that is, for example, by depletion of Trp in the medium, or by a combination of depletion of Trp in the medium and the addition of IAA to the medium. For example, expression may be induced by depletion of Trp in the medium, and the expression may further be enhanced by the addition of IAA to the medium. When expression is induced by depletion of Trp in the medium, the time at which Trp in the medium is depleted (the time of Trp depletion) may be regarded as the "time of inducing the expression". When the expression is induced by the addition IAA to the medium, the time at which IAA is added to the medium (the time of IAA addition) may be regarded as the "time of inducing the expression". When the expression is induced by a combination of depletion of Trp in the medium and addition of IAA to the medium, the time of Trp depletion or the time of IAA supply may be regarded as the "time of inducing the expression", or, the time of Trp depletion or the time of IAA addition, whichever comes later, may be regarded as the "time of inducing the expression". When the expression is induced by a combination of multiple requirements, expression may be induced by attaining all of those requirements after the start of the culture, or the expression may be induced by attaining at least one of those requirements after the start of the culture. That is, when the expression is induced by a combination of depletion of Trp in the medium and addition of IAA to the medium, it is acceptable that none of the requirements have been attained at the start of the culture and both the requirements are attained after the start of the culture, or it is also acceptable that either one of the requirements has been attained at the start of the culture and the other requirement is attained after the start of the culture. That is, in the latter case, for example, the cultivation can be started using a medium containing IAA and expression can be induced by depletion of Trp in the medium after the start of the culture, or cultivation can be started using a medium already depleted of Trp and expression is induced by addition of IAA to the medium after the start of the culture.

The phrase "depletion of Trp in a medium" can refer to when the Trp concentration in the medium is lower than a certain concentration. The term "certain concentration" in reference to the Trp concentration in the medium is not particularly limited, so long as expression can be induced. That is, the term "certain concentration" in reference to the Trp concentration in the medium may refer to, for example, a concentration at which expression is induced by depletion of Trp in the medium, or by a combination of depletion of Trp in the medium and addition of IAA to the medium. The term "certain concentration" in reference to the Trp concentration in the medium may refer to, specifically, for example, 50 mg/L, 40 mg/L, 30 mg/L, 20 mg/L, 10 mg/L, or 0 (zero). That is, the phrase "depletion of Trp in a medium" may refer to, specifically, for example, a condition where the Trp concentration in the medium is lower than 50 mg/L, lower than 40 mg/L, lower than 30 mg/L, lower than 20 mg/L, lower than 10 mg/L, or 0 (zero).

Trp in the medium may be depleted after the start of the culture. That is, the phrase "depletion of Trp in a medium" may refer to, specifically, a decrease in the Trp concentration in the medium from the certain concentration or higher to lower than the certain concentration. The certain concentration is as described above. That is, the cultivation step (step A) may include a culture period A1 and a culture period A2, wherein the culture period A2 occurs after the culture period A1, wherein the Trp concentration in the medium during the culture period A1 is the certain concentration or higher, for example, 50 mg/L or higher, and wherein the Trp concentration in the medium during the culture period A2 is lower than the certain concentration, for example, lower than 50 mg/L. In this case, the timepoint of switching from the culture period A1 to the culture period A2 may be regarded as the "time of inducing the expression". When expression is induced by a combination of depletion of Trp in the medium and supply of IAA to the medium, the timepoint of switching from the culture period A1 to the culture period A2 or the time of IAA addition may be regarded as the "time of inducing the expression", or, the timepoint of switching from the culture period A1 to the culture period A2 or the time of IAA addition, whichever comes later, may be regarded as the "time of inducing the expression". Methods for depleting Trp in the medium are not particularly limited. For example, due to the consumption of Trp in the medium by the bacterium, the Trp concentration in the medium decreases, and Trp in the medium is depleted. The Trp concentration in the medium may be or may not be the certain concentration or higher over the entire period of the period from the start of the culture to the time of Trp depletion, for example, over the entire period of the period before inducing the expression. Trp may or may not be present in the medium at the start of the culture. That is, for example, Trp may or may not be present in the medium at the certain concentration or higher at the start of the culture. Trp may be present in the medium at the certain concentration or higher at the start of the culture. When Trp is not present in the medium at the certain concentration or higher at the start of the culture, Trp can be added to the medium after the start of the culture until the Trp concentration in the medium is at the certain concentration or higher. Furthermore, Trp can be additionally supplied to the medium as required. Methods for adding Trp to the medium are not particularly limited. For example, Trp can be added to the medium by feeding a feed medium containing Trp to the medium. Trp can be added once or multiple times, or can be continuously added. The Trp concentration in the medium at the start of the culture, and the amount added and the timing of adding Trp to the medium after the start of the culture, is not particularly limited, so long as expression is induced. That is, whether Trp is present at the start of culture, and/or added after the start of the culture can be determined, for example, so that Trp in the medium is depleted at an appropriate time after the start of the culture. For example, Trp may be present in the medium at the start of the culture at a concentration appropriate for keeping the Trp concentration in the medium at the certain concentration or higher until the time of inducing the expression, or may be fed to the medium after the start of the culture at a feeding rate appropriate for keeping the Trp concentration in the medium at the certain concentration or higher until the time of inducing the expression. In addition, the use of Trp can be appropriately determined, for example, according to the various conditions such as the presence or absence of tryptophan auxotrophy of the chosen bacterium. The Trp concentration in the medium at the start of the culture, for example, may be the certain concentration or higher, e.g. 50 mg/L or higher, may be 5000 mg/L or lower, 4000 mg/L or lower, or 3000 mg/L or lower, or may be within a range defined by any combination of these ranges. The Trp concentration in the medium at the start of the culture may specifically be, for example, 50 mg/L to 5000 mg/L. The Trp concentration in the medium may or may not be lower than the certain concentration over the entire period of the period after Trp depletion, for example, over the entire period of the period after inducing the expression. The Trp concentration in the medium may be kept at lower than the certain concentration during the period of production of the fibroin-like protein.

Furthermore, depending on how expression is induced, it is also acceptable that the cultivation is started using a medium depleted of Trp and depletion of Trp can be continued. For example, when expression is induced by a combination of depletion of Trp in the medium and addition of IAA to the medium, it is acceptable that Trp in the medium is depleted after the start of the culture, or it is also acceptable that the cultivation is started using a medium depleted with Trp and depletion of Trp is continued. Also when expression is induced by a combination of depletion of Trp in the medium and addition of IAA to the medium, Trp may be depleted in the medium after the start of the culture as described above.

IAA can be added to the medium after the start of the culture. Methods for adding IAA to the medium are not particularly limited. For example, IAA can be added to the medium by feeding a feed medium containing IAA to the medium. IAA can be supplied once or multiple times, or can be supplied continuously. The amount of added IAA is not particularly limited, so long as expression is induced. That is, the amount of added IAA may be, for example, an amount at which expression is induced as a result of addition of IAA to the medium, or by a combination of depletion of Trp in the medium and addition of IAA to the medium. The added amount of IAA may be, for example, an amount such that the IAA concentration in the medium becomes a concentration typically used for inducing the trp promoter. The added amount of IAA may also be, specifically, for example, an amount such that the IAA concentration in the medium becomes 10 mg/L to 80 mg/L.

Furthermore, depending on how the expression is induced, it is also acceptable that IAA is added to the medium at the start of the culture, that is, IAA is present in the medium at the start of the culture. That is, depending on how expression is induced, for example, IAA may be present in the medium at the concentration exemplified above at the start of the culture. For example, when expression is induced by a combination of depletion of Trp in the medium and addition of IAA to the medium, IAA may be added to the medium after the start of the culture, or IAA may be present in the medium at the start of the culture. That is, when expression is induced by a combination of depletion of Trp in the medium and addition of IAA to the medium, for example, IAA may be present in the medium at the concentration exemplified above at the start of the culture, or IAA may be added to the medium after the start of the culture so that the IAA concentration in the medium becomes the concentration exemplified above. In any case, IAA can be additionally added to the medium as required.

When the expression is induced by a combination of depletion of Trp in the medium and addition of IAA to the medium, the order of depleting Trp and adding IAA to the medium is not particularly limited. That is, the timing of addition of IAA to the medium may be prior to, simultaneously with, or subsequent to the time of depletion of Trp in the medium.

As the medium, for example, usual media used for culture of bacteria such as *Escherichia coli* can be used as they are, or after appropriate modification. As the medium, for example, a liquid medium containing a carbon source, nitrogen source, phosphate source, sulfur source, and ingredients such as other various organic and inorganic ingredients as required can be used. Types and concentrations of the medium components may be appropriately chosen by those skilled in the art.

Specific examples of the carbon source can include, for example, saccharides such as glucose, fructose, sucrose, lactose, galactose, xylose, arabinose, blackstrap molasses, hydrolysate of starch, and hydrolysate of biomass, organic acids such as acetic acid, fumaric acid, citric acid, succinic acid, and malic acid, alcohols such as glycerol, crude glycerol, and ethanol, and aliphatic acids. As the carbon source, one kind of carbon source may be used, or two or more kinds of carbon sources may be used in combination. Among these, carbon sources other than organic acids can be used, and particular examples include saccharides and glucose. Ratio of glucose in the total carbon source may be, for example, 50% (w/w) or higher, 70% (w/w) or higher, 90% (w/w) or higher, 95% (w/w) or higher, or 100% (w/w).

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition product, ammonia, and urea. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components can include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

When an auxotrophic strain is used that requires a nutrient such as amino acids for growth, the required nutrient can be added to the medium. When a gene is introduced by using a vector carrying an antibiotic resistance gene, the corresponding antibiotic can be added to the medium.

The culture can be aerobically performed as, for example, an aeration culture or shaking culture. Oxygen concentration may be adjusted to, for example, 5 to 50%, or about 20 to 40%, of the saturated dissolved oxygen concentration. Culture temperature may be, for example, 20 to 45° C., 25 to 40° C., or 30 to 37° C. pH of the medium may be 5 to 9 during the culture. To adjust the pH, inorganic or organic acidic or alkaline substances such as calcium carbonate, ammonia gas, and aqueous ammonia can be used. The culture can be performed as batch culture, fed-batch culture, continuous culture, or a combination of these. The medium used at the time of the start of the culture can also be referred to as "starting medium". The medium added to a culture system, such as fermentation tank, used in fed-batch culture or continuous culture can also be referred to as "feed medium". To add a feed medium to a culture system used in fed-batch culture or continuous culture can also be referred to as to "feed". The culture may also be performed as separate pre-culture and main culture. The pre-culture may be performed by using, for example, a plate medium or liquid medium.

Each of the medium components may be contained in the starting medium, feed medium, or both. The types of components present in the starting medium may or may not be the same as those present in the feed medium. The concentrations of the components in the starting medium may or may not be the same as those in the feed medium. Furthermore, two or more kinds of feed media containing components of different types and/or different concentrations may be used. For example, when feeding is intermittently performed two or more times, types and/or concentrations of components contained in the respective feed media may or may not be the same.

The method as described herein is characterized in that accumulation of an organic acid at the time of inducing the expression of a fibroin-like protein is reduced. The expression "accumulation of an organic acid is reduced" can mean that the accumulation amount of the organic acid in the medium is smaller than the accumulation amount of the organic acid in the medium observed under control conditions, and may also mean that the organic acid does not accumulate at all in the medium. Examples of the organic acid can include, for example, acetic acid, citric acid, succinic acid, formic acid, and pyruvic acid. In the method, the accumulation amount of one kind of organic acid may be reduced, or the accumulation amounts of two or more kinds of organic acids may be reduced. Among those acids, the accumulation amount of at least acetic acid is reduced. The degree of the reduction is not particularly limited so long as production of the fibroin-like protein is improved compared with that observed under control conditions. The expression "accumulation of an organic acid is reduced" may also mean that the accumulation amount of the organic acid in the medium is, for example, 70% or less (lower), 50% or less (lower), 30% or less (lower), 20% or less (lower), 15% or less (lower), or 10% or less (lower) of the accumulation amount of the organic acid in the medium observed under control conditions. The expression "accumulation of an organic acid is reduced" may also mean that the accumulation amount of the organic acid in the medium (when there are two or more kinds of organic acids, the total amount of them) is, for example, 4.5 g/L or less (lower), 3.0 g/L or less (lower), 2.0 g/L or less (lower), 1.0 g/L or less (lower), 0.5 g/L or less (lower), 0.2 g/L or less (lower), 0.1 g/L or less (lower), or 0 (zero). The expression "accumulation of an organic acid is reduced" may also mean that the accumulation amount of acetic acid in the medium is, for example, 3.3 g/L or less (lower), 3.0 g/L or less (lower), 2.5 g/L or less (lower), 2.0 g/L or less (lower), 1.5 g/L or less (lower), 1.0 g/L or less (lower), 0.5 g/L or less (lower), 0.2 g/L or less (lower), 0.1 g/L or less (lower), or 0 (zero). The accumulation amount of an organic acid may be reduced as a result of, for example, reduction in the production amount of the organic acid, consumption of the organic acid once produced, or combination of these.

The term "control conditions" can refer to conditions under which accumulation of an organic acid is not reduced. Examples of the "control conditions" can include typical culture conditions for a strain of *Escherichia coli* under which an organic acid is by-produced. Examples of the "typical culture conditions for a strain of *Escherichia coli* under which an organic acid is by-produced" can include when the feeding rate of a carbon source into the culture system is higher than the consumption rate of the carbon source by the bacterium in the culture system, that is, in other words, when the culture is performed in the presence of a sufficient amount of the carbon source. When the culture is performed in the presence of a sufficient amount of carbon source, the concentration of the carbon source in the culture system is maintained to be high. Therefore, the expression "culture is performed in the presence of a sufficient amount of carbon source" may mean that the culture is performed so that the concentration of the carbon source in the medium is not lower than a certain concentration. The culture may be performed as batch culture, fed-batch culture, continuous culture, or a combination of these. Examples of the "conditions that the culture is performed in the presence of a sufficient amount of carbon source" can include, for example, when the glucose concentration in the medium is always not lower than a certain concentration from the start of the culture to immediately before inducing the expression. The term "immediately before inducing the expression" may refer to, for example, any time point within a period of from 1 hour before inducing the expression to the induction of the expression. The term "not lower than a certain concentration" may refer to, for example, a concentration of 0.5 g/L or higher, 1.0 g/L or higher, 2.0 g/L or higher, 3.0 g/L or higher, 5.0 g/L or higher, or 10.0 g/L or higher. Specific examples of the "typical culture condition under which an organic acid is by-produced" can include, for example, conditions that the culture is aerobically performed as batch culture by using a liquid medium containing a sufficient amount of glucose such as the control conditions described in the examples of this description. The "strain of *Escherichia coli*" is not particularly limited so long as it is an *Escherichia coli* strain not modified so that an organic acid-producing ability is reduced. Examples of the "strain of *Escherichia coli*" can include, when the bacterium as described herein is not modified so that an organic acid-producing ability is reduced, the bacterium as described herein; and when the bacterium as described herein is modified so that an organic acid-producing ability is reduced, a strain before the modification (i.e. a strain before being modified so that the organic acid-producing ability is reduced).

The expression "production of the fibroin-like protein is improved compared with that observed under control conditions" can mean that the value of a parameter that indicates the productivity of the fibroin-like protein is larger than that observed under the control conditions. The term "parameter that indicates the productivity of the fibroin-like protein" can refer to the accumulation amount of the fibroin-like protein relative to medium volume, the accumulation amount of the fibroin-like protein relative to cell weight, the cumulative productivity of the fibroin-like protein, the cumulative specific production rate (ρ-cumulative) of the fibroin-like protein, or a combination of these. The expression "production of the fibroin-like protein is improved compared with that observed under control conditions" may mean that, for example, the value of a parameter that indicates the productivity of the fibroin-like protein is 1.1 times or more, 1.2 times or more, 1.3 times or more, 1.4 times or more, or 1.5 times or more of that observed under the control conditions. The value of a parameter that indicates the productivity of fibroin-like protein may be larger than that observed under the control conditions in terms of, for example, the value observed at a predetermined time point during the period after inducing the expression, or the maximum value observed during the period after inducing the expression. The "predetermined time point" can be appropriately chosen depending on various conditions such as culture conditions. The term "predetermined time point" may refer to, for example, the time point at which accumulation of the fibroin-like protein stops. The term "time point at which accumulation of the fibroin-like protein stops" may refer to, for example, a time point at which increase ratio of the accumulation amount of the fibroin-like protein relative to cell weight becomes 10% or less (lower) per 4 to 12 hours. The term "time point at which accumulation of the fibroin-like protein stops" may also refer to, for example, 4 hours, 9 hours, 14 hours, 21.5 hours, 30 hours, 50 hours, 70 hours, or 100 hours after the induction of the expression, although it changes depending on the culture conditions.

The cumulative productivity of fibroin-like protein from the time of inducing the expression to a predetermined time point is calculated in accordance with the following equation.

$$\text{Cumulative productivity} = F/V/(T_1 - T_0)$$

F: Accumulation amount of fibroin-like protein (g)
V: Volume of medium (L)
$T_1$: Sampling time (predetermined time point)
$T_0$: Time of inducing expression The cumulative specific production rate of fibroin-like protein from the time of inducing the expression to a predetermined time point is calculated in accordance with the following equation.

$$\text{Cumulative specific production rate } (g/(g \cdot h)) = Pt/\int X t\, dt$$

t: Time after start of induction (h)
Pt: Accumulation of fibroin at t hours after start of induction
$\int X t\, dt$: Integrated cell amount from start of induction to t hours after start of induction (g·h)

Methods for reducing accumulation of the organic acid at the time of inducing the expression are not particularly limited.

Accumulation of the organic acid at the time of inducing the expression can be reduced by, for example, performing the culture under limitation of a carbon source (carbon source limitation) during the period before inducing the expression. The term "carbon source limitation" means that supply of a carbon source to a culture system is limited. By the carbon source limitation, the concentration of the carbon source in the culture system may be maintained to be low. That is, the term "carbon source limitation" may mean that, for example, the concentration of the carbon source in a medium is limited to be a certain concentration or lower. The value of the "certain concentration" is not particularly limited so long as production of the fibroin-like protein is improved compared with that observed under the control conditions. The term "certain concentration or lower" may refer to, for example, a concentration of 1.0 g/L or less (lower), 0.5 g/L or less (lower), 0.2 g/L or less (lower), 0.1 g/L or less (lower), or 0 (zero). The concentration of the carbon source may be limited to be a certain concentration or lower over the entire period before inducing the expression, or during only a partial period before inducing the expression. The length of the "partial period" is not particularly limited so long as production of the fibroin-like protein is improved compared with that observed under the control conditions. The term "partial period" may refer to, for example, a period of 15% or more, 30% or more, 50% or more, 70% or more, 90% or more, or 95% or more of the entire period before inducing the expression. The "partial period" may be, for example, the period from the start of the culture to the time of inducing the expression, the period from a time after the start of the culture to a time before inducing the expression, or the period from a time after the start of the culture to the time of inducing the expression. That is, the concentration of the carbon source in the medium may be limited to be the certain concentration or lower, for example, from an appropriate time after the start of the culture to the time of inducing the expression. The concentration of the carbon source may be or may not be constant over the entire period before inducing the expression. The carbon source can also be limited during the period after inducing the expression, in addition to the period before inducing the expression.

The carbon source can be limited by feeding a feed medium containing a carbon source so that the concentration of the carbon source in the medium is kept at the certain concentration or lower. The concentration of the carbon source in the medium can be kept at the certain concentration or lower by, for example, feeding the feed medium so that supply rate (feeding rate) of the carbon source into the culture system is lower than the consumption rate of the carbon source by the bacterium of the present invention in the culture system. The concentration of the carbon source in the feed medium and the feeding rate of the feed medium are not particularly limited so long as the concentration of the carbon source in the medium can be limited to be the certain concentration or lower. The concentration of the carbon source in the feed medium and the feeding rate of the feed medium can be appropriately chosen depending on various conditions such as culture conditions. The concentration of the carbon source in the feed medium or the feeding rate of the feed medium may be chosen so that, for example, the feeding rate of the carbon source (determined from the concentration of the carbon source in the feed medium and the feeding rate of the feed medium) is 1 to 100 g/hr, 1 to 70 g/hr, 1 to 40 g/hr, 1 to 30 g/hr, or 1 to 20 g/hr per 1 L of the culture medium at the time of the start of the culture. Both the concentration of the carbon source in the feed medium and the feeding rate of the feed medium may be or may not be constant over the period before inducing the expression.

Feeding of the feed medium may be performed continuously or intermittently. Feeding of the feed medium may be started at the time of the start of the culture, or may be started during the culture. Feeding of the feed medium may be started, for example, after the concentration of the carbon source in the medium becomes the certain concentration or lower, specifically, after the carbon source is depleted. When feeding is intermittently performed two or more times, the concentration of the carbon source in the fermentation medium can also be automatically maintained at a low level by controlling the feeding so that the second and following feedings are started when the carbon source in the fermentation medium is depleted in the non-feeding periods immediately before the respective feeding periods (U.S. Pat. No. 5,912,113). Depletion of the carbon source can be detected on the basis of, for example, elevation of pH, or elevation of dissolved oxygen concentration (U.S. Pat. No. 5,912,113).

The feeding of the feed medium is usually performed so that the carbon source is not depleted, or so that carbon source depletion does not continue. However, the carbon source may be temporarily depleted so long as production of the fibroin-like protein is improved compared with that observed under the control conditions. The term "temporarily" can refer to, for example, a period of 30% or less, 20% or less, 10% or less, or 5% or less of the entire period before inducing the expression. The concentration of the carbon source in the medium of 0 (zero) does not necessarily mean that the carbon source is depleted. That is, even if the concentration of the carbon source in the medium is maintained to be 0 (zero), if elevation of pH or elevation of dissolved oxygen concentration is not observed, the carbon source is not depleted. As such a case, there is assumed, for example, a case where although the feeding of the carbon source to the culture system is continued, the concentration of the carbon source in the medium is maintained to be 0 (zero) because of prompt consumption of the fed carbon source.

The concentration of the carbon source in the starting medium is not particularly limited so long as the carbon source limitation can be attained. The concentration of the carbon source in the starting medium may or may not be the certain concentration or lower. That is, it is acceptable that while the concentration of the carbon source in the starting medium is higher than the certain concentration, the carbon source in the starting medium is consumed during the culture and thereby the concentration of the carbon source becomes the certain concentration or lower. The concentration of the carbon source in the starting medium may be, for example, 100 g/L or less (lower), 70 g/L or less (lower), 50 g/L or less (lower), 30 g/L or less (lower), 20 g/L or less (lower), 10 g/L or less (lower), 5 g/L or less (lower), or 2 g/L or less (lower). The term "starting medium" may be read as "medium at the time of the start of the culture". Specifically, the term "medium at the time of the start of the culture" may refer to the culture medium immediately after inoculation.

Accumulation of the organic acid at the time of inducing the expression can also be reduced by, for example, using a strain modified so that the organic acid-producing ability is reduced.

Any one of such methods for reducing accumulation of the organic acid at the time of inducing the expression may be independently used, or two or more of them may be used in an appropriate combination.

By culturing the bacterium as described above, a fibroin-like protein can be accumulated in the medium and/or cells of the bacterium. The fibroin-like protein can be accumulated as, for example, inclusion bodies in the cells.

The fibroin-like protein can be collected and quantified by, for example, known methods for collecting and quantifying a heterogeneously expressed protein (see, for example, "Lecture of New Chemical Experiments, Protein VI, Synthesis and Expression", Ed. By Japanese Biochemical Society, Tokyo Kagaku Dojin, 1992, pp. 183-184).

Hereinafter, a procedure for collecting and quantifying a fibroin-like protein will be exemplified for when the fibroin-like protein is accumulated as inclusion bodies in the cells. First, the cells are collected from the culture medium by centrifugation, and then suspended in a buffer. The cell suspension is subjected to such a treatment as ultrasonication or French press to disrupt the cells. Before disrupting the cells, lysozyme may be added to the cell suspension at a final concentration of 0 to 200 mg/l, and the suspension may be incubated on ice for 30 minutes to 20 hours. Then, an insoluble fraction is obtained from the disrupted cell suspension as precipitates by low speed centrifugation (6000 to 15000 rpm, 5 to 10 minutes, 4° C.). The insoluble fraction is appropriately washed with a buffer as required. The number of times of washing is not be particularly limited, and may be, for example, once, twice, or 3 times or more. By suspending the insoluble fraction in a buffer, a suspension of the fibroin-like protein is obtained. As the buffer for suspending the cells or fibroin-like protein, a buffer in which the fibroin-like protein shows a low solubility can be used. Examples of such a buffer can include, for example, a buffer containing 20 mM Tris-HCl, 30 mM NaCl, and 10 mM EDTA, and a buffer containing 20 mM Tris-HCl and 30 mM NaCl. pH of the buffer may be, for example, usually 4 to 12, or 6 to 9. A solution of the fibroin-like protein can also be obtained by dissolving the insoluble fraction in an SDS solution or urea solution. The collected fibroin-like protein may contain such components as bacterial cells, medium components, and bacterial metabolic by-products, in addition to the fibroin-like protein. The fibroin-like protein may be purified to a desired degree. The amount of the fibroin-like protein can be determined, for example, as follows: a sample containing the fibroin-like protein such as suspension or solution is subjected to SDS-PAGE, and stained, and then, the amount of the fibroin-like protein can be determined on the basis of intensity of a band at the position corresponding to the molecular weight of the objective fibroin-like protein. The staining can be performed by CBB staining, fluorescence staining, silver staining, or the like. For the quantification, proteins of known concentrations can be used as the standards. Examples of such proteins can include, for example, albumin and a fibroin-like protein of which concentration is separately determined.

The fibroin-like protein obtained as described above can be subjected to fibrillation or the like as required, and then used. Fibrillation of a fibroin-like protein can be performed by, for example, a known method. Specifically, fibrillation of a fibroin-like protein can be performed with reference to, for example, the descriptions concerning fibrillation of polypeptides originating in large spigot drag line proteins described in WO2012/165476.

EXAMPLES

Hereinafter, the present invention will be more specifically explained with reference to the following non-limiting examples.

Reference Example 1: Construction of Fibroin-Like Protein-Producing Strain

The strains, plasmid, and gene used for production of a fibroin-like protein in the Examples (Examples 1-3) are as follows.

Host: *Escherichia coli* Rosetta(DE3) and *Escherichia coli* Rosetta(DE3)ΔrecAΔtrpEDCBA Plasmid: pP$_{trp}$-GEN202 lacI::trpR Fibroin-like protein gene: Gene having the nucleotide sequence shown as SEQ ID NO: 1

The *Escherichia coli* Rosetta(DE3)ΔrecA strain, which is deficient in the recA gene, was constructed from *Escherichia coli* Rosetta(DE3) as the parent strain via the following procedure. Specifically, P1 transduction was carried out with the *Escherichia coli* BLR(DE3) strain (F$^-$ ompT hsdS$_B$ (r$_B^-$m$_B^-$) gal dcm (DE3) Δ(srl-recA)306::Tn10 (Tet$^R$)) as the donor and the *Escherichia coli* Rosetta(DE3) strain as the recipient, to obtain a Tet-resistant clone, which was designated as the strain Rosetta(DE3)ΔrecA.

The *Escherichia coli* Rosetta(DE3)ΔrecAΔtrpEDCBA strain, which is a tryptophan auxotrophic strain deficient in the recA gene and the Trp biosynthesis operon trpEDCBA, was constructed from *Escherichia coli* Rosetta(DE3) as the parent strain via the following procedure. Specifically, PCR reaction was carried out by using the oligonucleotides shown in SEQ ID NOS: 10 and 11 as the primers, the genomic DNA of an *Escherichia coli* strain having the attL-Km$_r$-attL sequence (SEQ ID NO: 12) on the chromosome thereof as the template, and KOD FX DNA polymerase (TOYOBO), to obtain a DNA fragment of about 1.6 kb containing the attL-Km$^r$-attL sequence. Km$^r$ is a kanamycin resistance gene derived from the *Escherichia coli* Bacterial transposon Tn9. The PCR reaction consisted of 25 cycles, each of which cycles consisted of reactions of 94° C. for 10 sec, 55° C. for 30 sec, and 68° C. for 1 min and 30 sec. The obtained DNA fragment was purified with S-400 HRColumns (GE Healthcare). The obtained DNA fragment was used to replace the trpEDCBA operon region of the *Escherichia coli* MG1655 strain with the kanamycin resistance gene on this DNA fragment by Red-driven integration (Datsenko, K. A, and Wanner, B. L. Proc. Natl. Acad. Sci. USA. 97:6640-6645 (2000)), to thereby construct the *Escherichia coli* MG1655 trpEDCBA::Km$^r$ strain. Then, P1 transduction was carried out with the MG1655 trpEDCBA::Km$^r$ strain as the donor and the *Escherichia coli* Rosetta (DE3) as the recipient, to obtain the *Escherichia coli* Rosetta (DE3) trpEDCBA::Km$^r$ strain, of which the trpEDCBA operon region was replaced with the kanamycin resistance gene. Then, the kanamycin resistance gene was removed from the Rosetta(DE3) trpEDCBA::Km$^r$ strain by using the pMW-int-xis plasmid (WO2007/037460), to obtain the *Escherichia coli* Rosetta(DE3)ΔtrpEDCBA strain, which is auxotrophic for tryptophan. Then, the recA gene of the *Escherichia coli* Rosetta(DE3)ΔtrpEDCBA strain was deleted in the same manner as described above, i.e. P1 transduction using the BLR(DE3) strain as the donor, to construct the *Escherichia coli* Rosetta(DE3) ΔrecAΔtrpEDCBA strain.

pP$_{trp}$-GEN202 lacI::trpR is a plasmid for a constitutive expression of a trp repressor gene, and for an induced expression of the fibroin-like protein gene from a trp promoter. The nucleotide sequence of the fibroin-like protein gene is shown in SEQ ID NO: 1, and the amino acid sequence of the fibroin-like protein encoded by the gene is shown in SEQ ID NO: 2. pP$_{trp}$-GEN202 lacI::trpR can be constructed from the pET22b(+) vector (Novagen) via the following procedure.

The pET22b(+) vector is digested with the restriction enzymes NdeI and EcoRI, and then inserted with the fibroin-like protein gene (SEQ ID NO: 1) by using DNA Ligation Kit (TaKaRa), to obtain a pET22b(+) vector containing the fibroin-like protein gene.

The trp promoter sequence shown in SEQ ID NO: 6 is inserted upstream of the fibroin-like protein gene on the obtained vector. Specifically, PCR reaction was carried out by using the oligonucleotides shown in SEQ ID NOS: 13 and 14 as the primers and KOD FX DNA polymerase (TOYOBO) without the template, to obtain a DNA fragment of 95 bp. The PCR reaction consists of 25 cycles, each of which cycles consists of reactions of 94° C. for 10 sec, 55° C. for 30 sec, and 68° C. for 1 min. The obtained DNA fragment was purified with S-400 HRColumns (GE Healthcare). The pET22b(+) vector containing the fibroin-like protein gene is digested with the restriction enzymes BglII and NdeI, and then ligated with the DNA fragment by using in-fusion cloning kit (Clontech). This product is used to transform *Escherichia coli* JM109 (TaKaRa), and plasmids are harvested, to obtain pP$_{trp}$-GEN202.

A lacI region (inherently contained in the pET22b(+) vector) on pP$_{trp}$-GEN202 is replaced with a region of SEQ ID NO: 7 containing a promoter (bla promoter) of an ampicillin resistance gene (derived from *Escherichia coli* Bacterial transposon Tn3) and the trp repressor gene (trpR gene; SEQ ID NO: 8) located immediately downstream of the region. Specifically, PCR reaction is carried out by using the oligonucleotides shown in SEQ ID NOS: 15 and 16 as the primers, the genomic DNA of the *Escherichia coli* MG1655 strain as the template, and KOD FX DNA polymerase (TOYOBO), to obtain a DNA fragment of 466 bp (1st PCR product). PCR consists of 25 cycles, each of which cycles consists of reactions of 94° C. for 10 sec, 55° C. for 30 sec, and 68° C. for 50 sec. The 1st PCR product is purified with S-400 HRColumns (GE Healthcare). Then, PCR reaction is carried out by using the oligonucleotides shown in SEQ ID NOS: 16 and 17 as the primers, the 1st PCR product as the template, and KOD FX DNA polymerase (TOYOBO), to obtain a DNA fragment of 522 bp (2nd PCR product). PCR consists of 25 cycles, each of which cycles consists of reactions of 98° C. for 10 sec and 68° C. for 40 sec. The 2nd PCR product is purified with S-400 HRColumns (GE Healthcare). Then, PCR reaction is carried out by using the oligonucleotides shown in SEQ ID NOS: 16 and 18 as the primers, the 2nd PCR product as the template, and KOD FX DNA polymerase (TOYOBO), to obtain a DNA fragment of 578 bp (3rd PCR product). The PCR reaction consists of 25 cycles, each of which cycles consists of reactions of 98° C. for 10 sec and 68° C. for 40 sec. The 3rd PCR product is purified with S-400 HRColumns (GE Healthcare). Then, PCR reaction is carried out by using the oligonucleotides shown in SEQ ID NOS: 16 and 19 as the primers, the 3rd PCR product as the template, and KOD FX DNA polymerase (TOYOBO), to obtain a DNA fragment of 537 bp (4th PCR product). The PCR reaction consists of 25 cycles, each of which cycles consists of reactions of 94° C. for 30 sec, 60° C. for 30 sec, and 68° C. for 1 min. The 4th PCR product is purified with S-400 HRColumns (GE Healthcare). $pP_{trp}$-GEN202 is digested with the restriction enzymes SphI and PshAI, and then ligated with the 4th PCR product by using in-fusion cloning kit (Clontech). This product is used to transform *Escherichia coli* JM109 (TaKaRa), and plasmids are harvested, to obtain $pP_{trp}$-GEN202 lacI::trpR.

The *Escherichia coli* strains Rosetta(DE3)ΔrecA and Rosetta(DE3)ΔrecAΔtrpEDCBA can be transformed with $pP_{trp}$-GEN202 lacI::trpR, to thereby obtain fibroin-like protein-producing bacteria Rosetta(DE3)ΔrecA/$pP_{trp}$-GEN202 lacI::trpR and Rosetta(DE3)ΔrecAΔtrpEDCBA/$pP_{trp}$-GEN202 lacI::trpR. Hereinafter, Rosetta(DE3)ΔrecA/$pP_{trp}$-GEN202 lacI::trpR is referred to as "tryptophan prototrophic strain (strain not auxotrophic for tryptophan)", and Rosetta (DE3)ΔrecAΔtrpEDCBA/$pP_{trp}$-GEN202 lacI::trpR is referred to as "tryptophan auxotrophic strain".

Reference Example 2: Preparation of Seed Culture Broth

The fibroin-like protein-producing bacteria were each inoculated into 300 ml of the medium for seed culture shown in Table 1, which was contained in a jar fermenter, at an absorbance at 620 nm of 0.005. The absorbance of the culture broth was measured with a spectrophotometer UV-mini1240 (Shimadzu). Culture was performed with keeping temperature of the culture broth at 37° C., performing aeration with air disinfected with a filter at 1 vvm, stirring at 1500 rpm, and maintaining pH of the culture broth to be constant at 6.7 by appropriately blowing ammonia gas into the culture broth. When glucose in the culture broth was completely consumed, the culture was terminated, to obtain a seed culture broth.

TABLE 1

| Medium for seed culture (per 1 L) | |
| --- | --- |
| Glucose | 40.0 g |
| $MgSO_4 \cdot 7H_2O$ | 1.0 g |
| CSL | 1.0 g (as Nitrogen amount) |
| Tryptophan | 1.0 g |
| $KH_2PO_4$ | 2.0 g |
| $FeSO_4 \cdot 7H_2O$ | 10.0 mg |
| $MnSO_4 \cdot 5H_2O$ | 10.0 mg |
| Isoleucine | 1.0 g |
| GD-113 (antifoam) | 0.1 mL |

Stock solutions were prepared for glucose and $MgSO_4 \cdot 7H_2O$ as division A, CSL (corn steep liquor) as division B, tryptophan as division C, and the other ingredients as division D. Then, the stock solutions of the divisions A and D were each sterilized in an autoclave at 120° C. for 20 minutes. pH of the stock solution of the division B was lowered to 2 by using sulfuric acid, and the solution was subjected to a heat treatment at 80° C. for 60 minutes, and then sterilized in an autoclave at 120° C. for 20 minutes. The stock solution of the division C was sterilized with a 0.22 µm filter. Then, the stock solutions of the divisions A, B, C, and D were mixed, and ampicillin was added to the mixture at a concentration of 100 mg/L, to obtain the medium for seed culture.

Example 1: Production of Fibroin-Like Protein by Tryptophan Auxotrophic Strain Under Condition of Performing Saccharide Limitation Before Inducing Expression (1) Production of Fibroin-Like Protein Under Condition of Performing Culture with Sufficient Amount of Saccharide so that Tryptophan in Culture Broth is Depleted Culture was performed via the following procedure by using the tryptophan auxotrophic strain with a sufficient amount of glucose so that tryptophan in the culture broth was depleted. In Example 1, this condition is also referred to as "control condition".

A seed culture broth was prepared by the method described in Reference Example 2. A 45-ml aliquot of the seed culture broth was inoculated into 255 ml of the production medium shown in Table 2 in a jar fermenter. Culture was performed with keeping temperature of the culture broth at 37° C., performing aeration with air disinfected with a filter at 1 vvm, stirring at 700 rpm, and maintaining pH of the culture broth to be constant at 6.9 by appropriately blowing ammonia gas into the culture broth. The dissolved oxygen concentration in the culture broth was measured with a dissolved oxygen concentration sensor, OxyProbe (registered trademark) Dissolved Oxygen Sensors (Broadley-James), and was kept at 20% or higher of the saturated dissolved oxygen concentration by increasing the stirring rate up to 2000 rpm as required.

TABLE 2

| Production medium (per 1 L) | |
| --- | --- |
| Glucose | 45.0 g |
| $MgSO_4 \cdot 7H_2O$ | 2.4 g |
| CSL | 1.0 g (as Nitrogen amount) |
| $KH_2PO_4$ | 9.0 g |
| $FeSO_4 \cdot 7H_2O$ | 40.0 mg |
| $MnSO_4 \cdot 5H_2O$ | 40.0 mg |
| $CaCl_2 \cdot 2H_2O$ | 40.0 mg |
| Isoleucine | 3.0 g |
| GD-113 (antifoam) | 0.1 mL |

Stock solutions were prepared for glucose and $MgSO_4 \cdot 7H_2O$ as division A, CSL as division B, and the other ingredients as division C. Then, the stock solutions of the divisions A and C were each sterilized in an autoclave at 120° C. for 20 minutes. pH of the stock solution of the division B was lowered to 2 by using sulfuric acid, and the solution was subjected to a heat treatment at 80° C. for 60 minutes, and then sterilized in an autoclave at 120° C. for 20 minutes. Then, the stock solutions of the divisions A, B, and C were mixed, and ampicillin was added to the mixture at a concentration of 100 mg/L, to obtain the production medium.

Before starting the culture or at the 5th hour of the culture, the IAA (3-beta-indoleacrylic acid) solution shown in Table 3 was added to the production medium at a concentration of 25 mg/L. Then, at the timepoint when glucose in the production medium was completely consumed, the feed medium shown in Table 4 was started to be added at a flow rate of 2.6 ml/h, and the culture was continued till the 32th hour.

TABLE 3

| IAA solution (per 1 L) | |
| --- | --- |
| IAA | 25 g |

IAA was dissolved in EtOH and sterilized with a 0.22 μm filter.

TABLE 4

| Feed medium (per 1 L) | |
| --- | --- |
| Glucose | 700 g |

The solution was sterilized in an autoclave at 120° C. for 20 minutes, and added with ampicillin at a concentration of 100 mg/L, to obtain the feed medium.

(2) Production of Fibroin-Like Protein Under Condition of Performing Saccharide Limitation Culture Before Tryptophan in Culture Broth is Depleted Culture was performed via the following procedure by using the tryptophan auxotrophic strain under a condition of keeping the glucose concentration at a low level before tryptophan in the culture broth was depleted. In Example 1, this condition is also referred to as "saccharide limitation condition".

The culture was performed with the production medium shown in Table 5 in the same manner as Example 1(1).

TABLE 5

| Production medium (per 1 L) | |
| --- | --- |
| Glucose | 45.0 g |
| $MgSO_4 \cdot 7H_2O$ | 2.4 g |
| CSL | 1.0 g (as Nitrogen amount) |
| Tryptophan | 1.0 g |
| $KH_2PO_4$ | 9.0 g |
| $FeSO_4 \cdot 7H_2O$ | 40.0 mg |
| $MnSO_4 \cdot 5H_2O$ | 40.0 mg |
| $CaCl_2 \cdot 2H_2O$ | 40.0 mg |
| Isoleucine | 3.0 g |
| GD-113 | 0.1 mL |

Stock solutions were prepared for glucose and $MgSO_4 \cdot 7H_2O$ as division A, CSL as division B, tryptophan as division C, and the other ingredients as division D. Then, the stock solutions of the divisions A and D were each sterilized in an autoclave at 120° C. for 20 minutes. pH of the stock solution of the division B was lowered to 2 by using sulfuric acid, and the solution was subjected to a heat treatment at 80° C. for 60 minutes, and then sterilized in an autoclave at 120° C. for 20 minutes. The stock solution of the division C was sterilized with a 0.22 μm filter. Then, the stock solutions of the divisions A, B, C, and D were mixed, and ampicillin was added to the mixture at a concentration of 100 mg/L, to obtain the production medium.

The IAA solution and the feed medium were added in the same manner as Example 1(1), and the culture was continued till the 32th hour.

(3) Analysis

In the culture of the sections (1) and (2) described above, the culture broth was sampled in an appropriate volume during the culture and after the end of the culture, and subjected to the analysis described below.

Figure 1B:
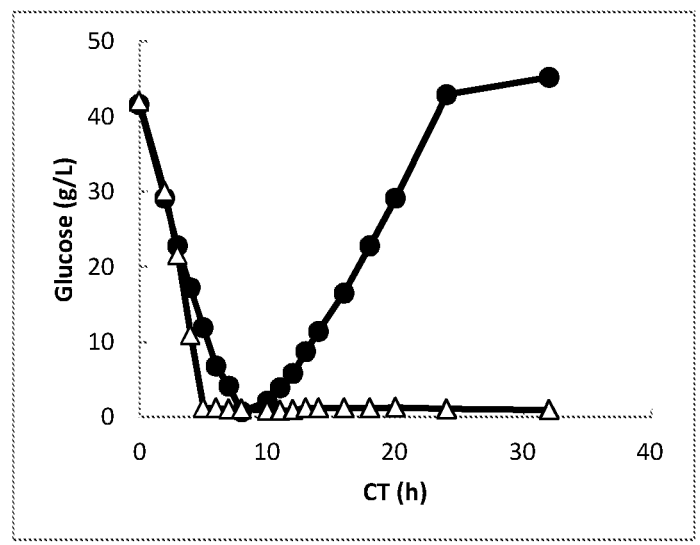

The glucose concentration in the culture broth was measured by using a multifunctional biosensor BF-5 (Oji Scientific Instruments). The measurement results are shown in FIG. 1.

Figure 2A:
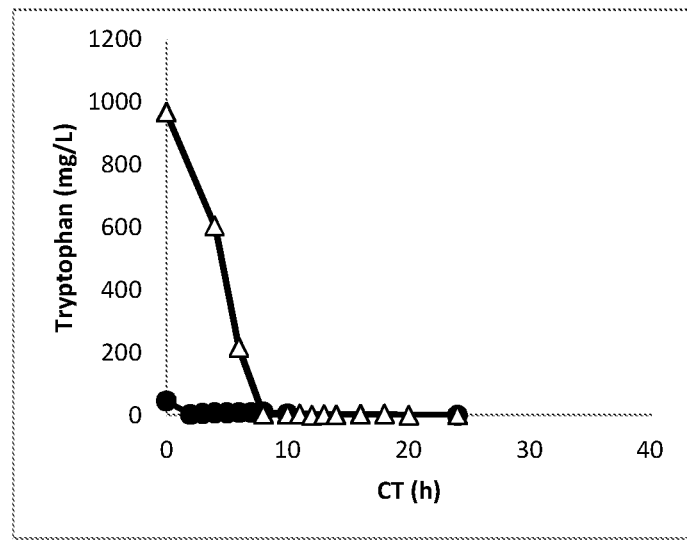
FIGS. 2A and 2B show graphs showing change of the tryptophan concentration over time when adding IAA solution before the start of culture (2A) and after 5 hours of culture (2B). The symbols • indicate the results obtained with the control condition, and the symbols Δ indicate the results obtained with the saccharide-limited condition.
Figure 2B:
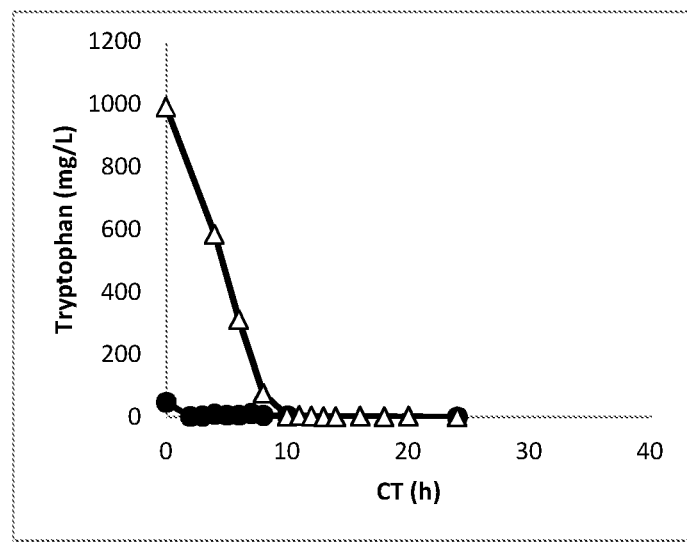
Figure 3A:
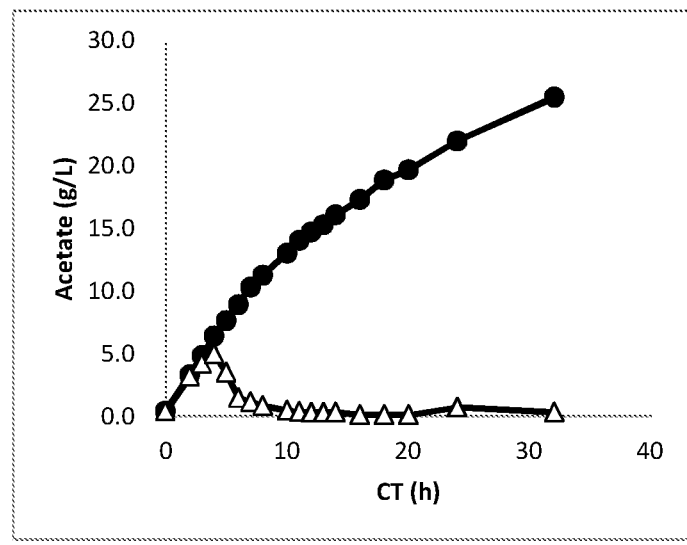
FIGS. 3A and 3B show graphs showing change of the acetic acid concentration over time when adding IAA solution before the start of culture (3A) and after 5 hours of culture (3B). The symbols • indicate the results obtained with the control condition, and the symbols Δ indicate the results obtained with the saccharide-limited condition.
Figure 3B:
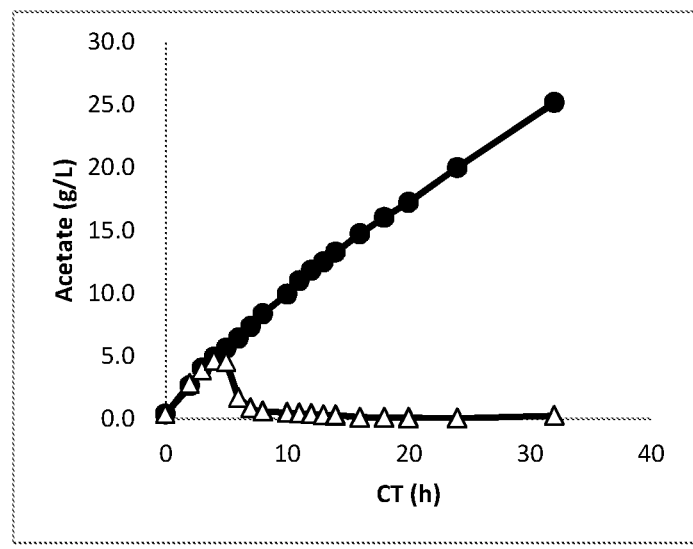

The tryptophan concentration in the culture broth was measured by HPLC under the following conditions. The measurement results are shown in FIG. 2.
 HPLC: L-2400 (HITACHI)
 Column: YMC-Pack ODS-AQ 150×6.0 mm I.D., S-5 m, 12 nm
 Temperature: 40° C.
 Flow rate: 1.0 mL/min
 UV detection: 280 nm
 Injection volume: 10 μL
 Mobile phase: Water:Methanol=2:1
 Elution: Isocratic elution The acetic acid concentration in the culture broth was measured by HPLC under the following conditions. The measurement results are shown in FIG. 3.
 HPLC: CDD-10A VP (Shimadzu)
 Column: Packed column Simpack SCR-102 (H)×2 (serially connected)
 Temperature: 40° C.
 Flow rate: 0.8 mL/min
 Conditions: polarity, +; Response, Slow; Gain, 0.1 μS/cm; range, 1

Figure 4A:
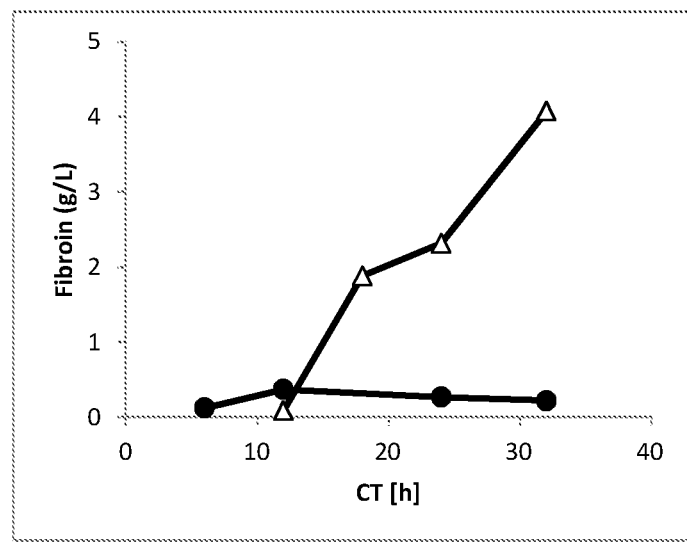
FIGS. 4A and 4B show graphs showing change of the accumulation amount of fibroin-like protein over time when adding IAA solution before the start of culture (4A) and after 5 hours of culture (4B). The symbols • indicate the results obtained with the control condition, and the symbols Δ indicate the results obtained with the saccharide-limited condition.
Figure 4B:
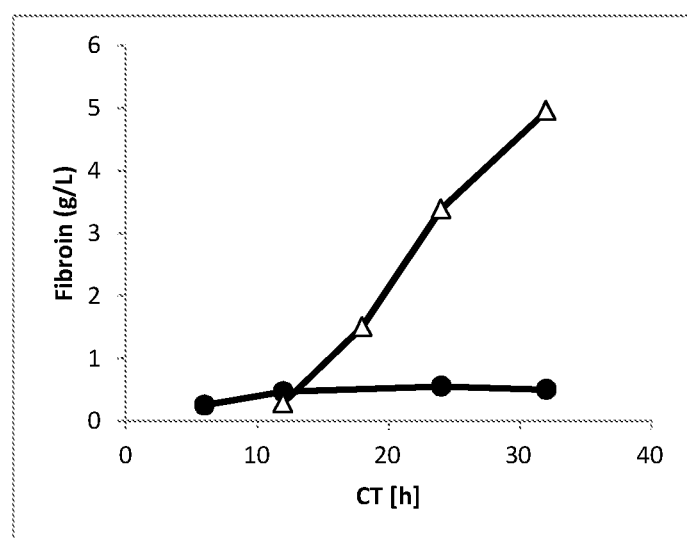
Figure 5:
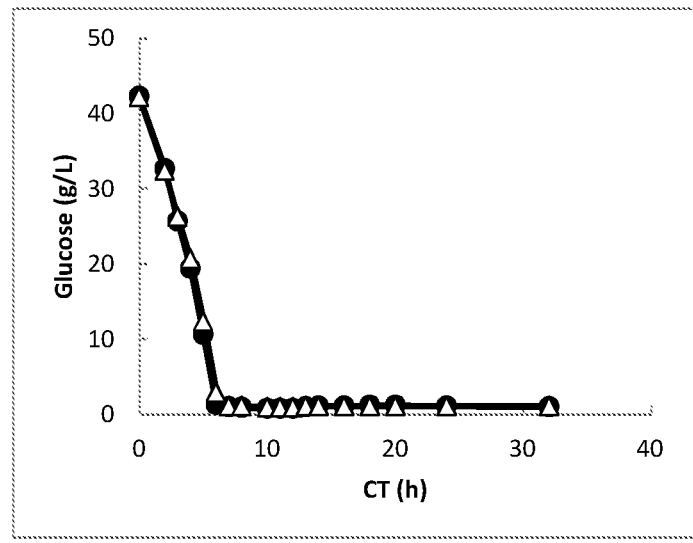
FIG. 5 shows a graph showing change of the glucose concentration over time. The symbols • indicate the results obtained with the control condition, and the symbols Δ indicate the results obtained with the saccharide-limited condition.
Figure 6:
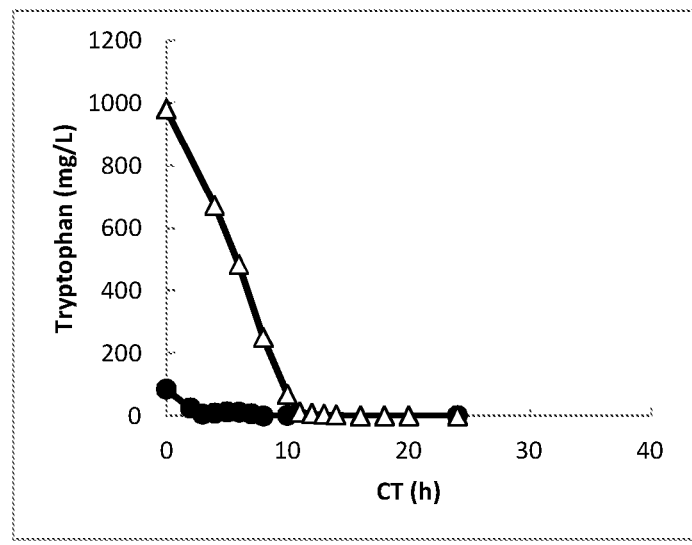
FIG. 6 shows a graph showing change of the tryptophan concentration over time. The symbols • indicate the results obtained with the control condition, and the symbols Δ indicate the results obtained with the saccharide-limited condition.
Figure 7:
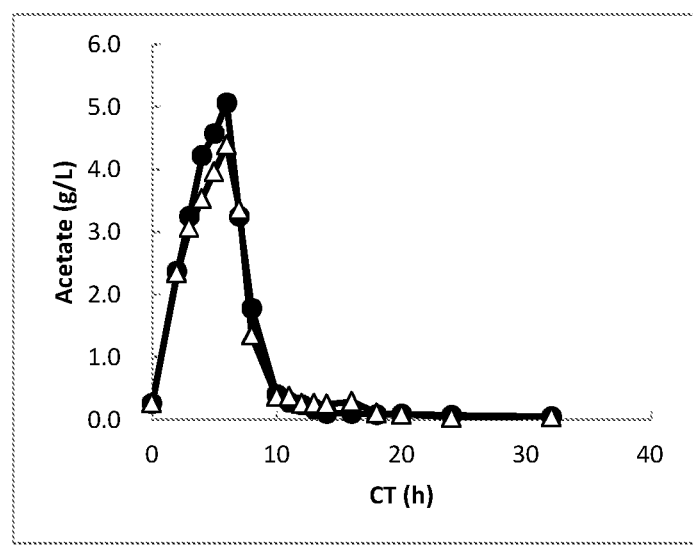
FIG. 7 shows a graph showing change of the acetic acid concentration over time. The symbols • indicate the results obtained with the control condition, and the symbols Δ indicate the results obtained with the saccharide-limited condition.
Figure 8:
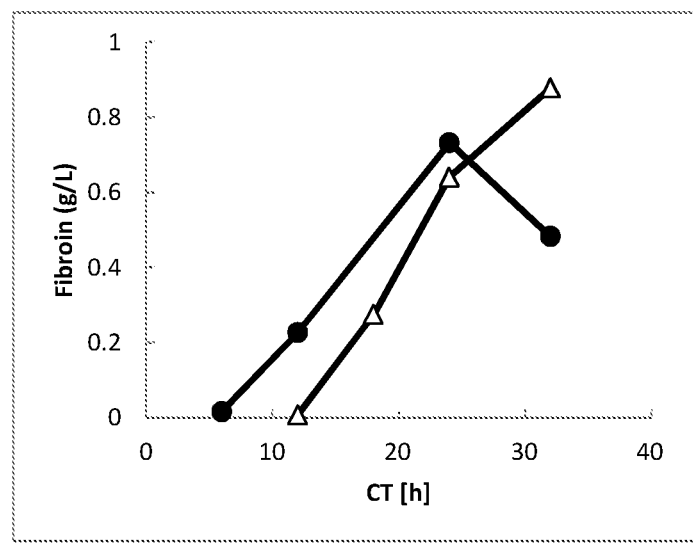
FIG. 8 shows a graph showing change of the accumulation amount of fibroin-like protein over time. The symbols • indicate the results obtained with the control condition, and the symbols Δ indicate the results obtained with the saccharide-limited condition.

The fibroin-like protein produced was appropriately quantified. The measurement results are shown in FIG. 4.

(A) Condition of Adding IAA Solution Before Starting Culture

Under the control condition, the tryptophan concentration in the culture broth was decreased to below 50 mg/L at the 2nd hour of the culture. At this timepoint, the glucose concentration was 28.9 g/L, which means that a sufficient amount of the saccharide was present, and the accumulation amount of acetic acid was 3.3 g/L. By contrast, under the saccharide limitation condition, glucose in the production medium was completely consumed at the 5th hour of the culture, and thereafter, the glucose concentration was kept at 1.0 g/L or lower. Under the saccharide limitation condition, the tryptophan concentration in the culture broth was decreased to below 50 mg/L at the 8th hour of the culture. At this timepoint, the accumulation amount of acetic acid was decreased to 0.8 g/L, which was 30% or lower of that observed for the control condition. The accumulation amount of the fibroin-like protein at the end of the culture was increased to 4.1 g/L under the saccharide limitation condition, while it was 0.2 g/L under the control condition.

(B) Condition of Adding IAA Solution at 5th Hour of Culture

Under the control condition, the tryptophan concentration in the culture broth was decreased to below 50 mg/L at the 2nd hour of the culture. At this timepoint, the glucose concentration was 29.1 g/L, which means that a sufficient amount of the saccharide was present, and the accumulation amount of acetic acid was 3.3 g/L. By contrast, under the saccharide limitation condition, glucose in the production medium was completely consumed at the 5th hour of the culture, and thereafter, the glucose concentration was kept at 1.0 g/L or lower. Under the saccharide limitation condition, the tryptophan concentration in the culture broth was decreased to below 50 mg/L at the 10th hour of the culture.

At this timepoint, the accumulation amount of acetic acid was decreased to 0.5 g/L, which was 15% or lower of that observed for the control condition. The accumulation amount of the fibroin-like protein at the end of the culture was increased to 5.0 g/L under the saccharide limitation condition, while it was 0.5 g/L under the control condition.

From these results, it was revealed that, when using a tryptophan auxotrophic strain, by performing a saccharide limitation culture before tryptophan in the culture broth was depleted, the accumulation amount of acetic acid at the time of tryptophan depletion is decreased and the accumulation amount of a fibroin-like protein is improved regardless of means for addition of an IAA solution. Hence, it was suggested that by reducing the accumulation amount(s) of organic acid(s) at the time of inducing the expression, production of a fibroin-like protein is improved.

Example 2: Production of Fibroin-Like Protein by Tryptophan Prototrophic Strain (Strain not Auxotrophic for Tryptophan) Under Condition of Performing Saccharide Limitation Before Inducing Expression (1) Production of fibroin-like protein under condition of performing culture with sufficient amount of saccharide so that tryptophan in culture broth is depleted Culture was performed via the following procedure by using the tryptophan prototrophic strain with a sufficient amount of glucose so that tryptophan in the culture broth was depleted. In Example 2, this condition is also referred to as "control condition".

A seed culture broth was prepared by the method described in Reference Example 2. A 45-ml aliquot of the seed culture broth was inoculated into 255 ml of the production medium shown in Table 2 in a jar fermenter. Culture was performed with keeping temperature of the culture broth at 37° C., performing aeration with air disinfected with a filter at 1 vvm, stirring at 700 rpm, and maintaining pH of the culture broth to be constant at 6.9 by appropriately blowing ammonia gas into the culture broth. The dissolved oxygen concentration in the culture broth was measured with a dissolved oxygen concentration sensor, OxyProbe (registered trademark) Dissolved Oxygen Sensors (Broadley-James), and was kept at 20% or higher of the saturated dissolved oxygen concentration by increasing the stirring rate up to 2000 rpm as required.

At the 6.5th hour of the culture, the IAA solution shown in Table 3 was added at a concentration of 25 mg/L. Then, at the timepoint when glucose in the production medium was completely consumed, the feed medium shown in Table 4 was started to be added at a flow rate of 2.6 ml/h, and the culture was continued till the 32th hour.

(2) Production of Fibroin-Like Protein Under Condition of Performing Saccharide Limitation Before Tryptophan in Culture Broth is Depleted Culture was performed via the following procedure by using the tryptophan prototrophic strain under a condition of keeping the glucose concentration in the culture broth at a low level. In Example 2, this condition is also referred to as "saccharide limitation condition".

The culture was performed with the production medium shown in Table 5 in the same manner as Example 2(1). In addition, the IAA solution and the feed medium were added in the same manner as Example 2(1), and the culture was continued till the 32th hour.

(3) Analysis

In the culture of the sections (1) and (2) described above, the culture broth was sampled in an appropriate volume during the culture and after the end of the culture, and the glucose concentration, tryptophan concentration, acetic acid concentration, and fibroin-like protein concentration in the culture broth were measured in the same manner as Example 1(3). The measurement results are shown in FIGS. 5-8.

Under the control condition, the tryptophan concentration in the culture broth was decreased to below 50 mg/L at the 2nd hour of the culture. At this timepoint, the glucose concentration was 32.7 g/L, which means that a sufficient amount of the saccharide was present, and the accumulation amount of acetic acid was 2.4 g/L. By contrast, under the saccharide limitation condition, glucose in the production medium was completely consumed at the 6.5th hour of the culture, and thereafter, the glucose concentration was kept at 1.0 g/L or lower. Under the saccharide limitation condition, the tryptophan concentration in the culture broth was decreased to below 50 mg/L at the 11th hour of the culture. At this timepoint, the accumulation amount of acetic acid was decreased to 0.4 g/L, which was 20% or lower of that observed for the control condition. The accumulation amount of the fibroin-like protein at the end of the culture was increased to 0.9 g/L under the saccharide limitation condition, while it was 0.5 g/L under the control condition.

From these results, it was revealed that, when using a tryptophan prototrophic strain, by performing a culture under saccharide limitation before tryptophan in the culture broth was depleted, the accumulation amount of acetic acid at the time of tryptophan depletion is decreased and the accumulation amount of a fibroin-like protein is improved. Hence, it was suggested that by reducing the accumulation amount(s) of organic acid(s) at the time of inducing the expression, production of a fibroin-like protein is improved.

Example 3: Production of Fibroin-Like Protein Under Condition of not Adding IAA

Culture was performed via the following procedure by using the tryptophan prototrophic strain without adding IAA so that tryptophan in the culture broth was depleted.

A seed culture broth was prepared by the method described in Reference Example 2. A 45-ml aliquot of the seed culture broth was inoculated into 255 ml of the production medium shown in Table 5 in a jar fermenter. Culture was performed with keeping temperature of the culture broth at 37° C., performing aeration with air disinfected with a filter at 1 vvm, stirring at 700 rpm, and maintaining pH of the culture broth to be constant at 6.9 by appropriately blowing ammonia gas into the culture broth. The dissolved oxygen concentration in the culture broth was measured with a dissolved oxygen concentration sensor, OxyProbe (registered trademark) Dissolved Oxygen Sensors (Broadley-James), and was kept at 20% or higher of the saturated dissolved oxygen concentration by increasing the stirring rate up to 2000 rpm as required.

At the timepoint when glucose in the production medium was completely consumed, the feed medium shown in Table 4 was started to be added at a flow rate of 2.6 ml/h, and the culture was continued till the 48th hour.

Figure 9:
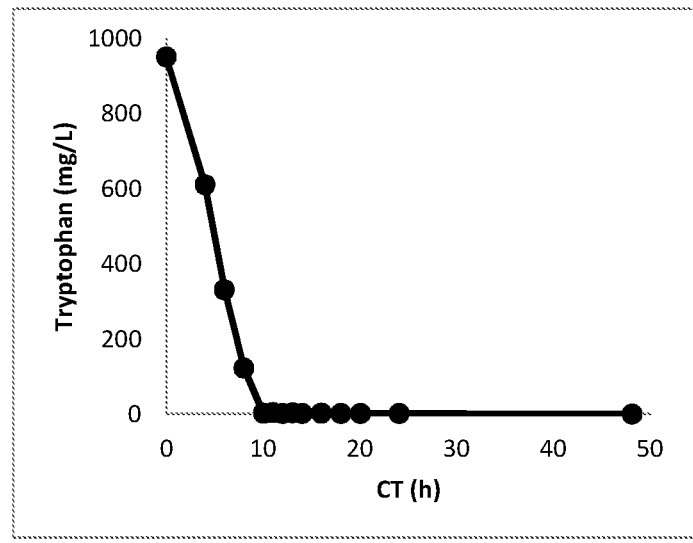
FIG. 9 shows a graph showing change of the tryptophan concentration over time.
Figure 10:
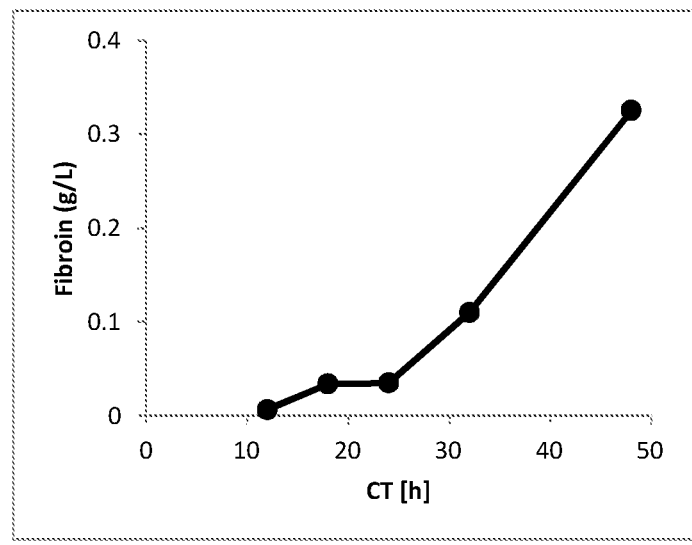
FIG. 10 shows a graph showing change of the accumulation amount of fibroin-like protein over time.

The culture broth was sampled in an appropriate volume during the culture and after the end of the culture, and the tryptophan concentration and fibroin-like protein concentration in the culture broth were measured in the same manner as Example 1(3). The measurement results are shown in FIGS. 9 and 10.

The tryptophan concentration in the culture broth was decreased to below 50 mg/L at the 10th hour of the culture. At this timepoint, the fibroin-like protein was started to be produced, and 0.3 g/L accumulation thereof was observed at the end of the culture.

From these results, it was revealed that, even without adding IAA, the expression of a fibroin-like protein is induced by depletion of tryptophan in the culture broth.

INDUSTRIAL APPLICABILITY

According to the present invention, a fibroin-like protein can be efficiently produced.

EXPLANATION OF SEQUENCE LISTING

SEQ ID NO: 1, Nucleotide sequence of fibroin-like protein gene used in Examples

SEQ ID NO: 2, Amino acid sequence of protein encoded by the fibroin-like protein gene used in Examples SEQ ID NO: 3, Amino acid sequence of ADF3 (partial) of *Araneus diadematus*

SEQ ID NO: 4, Nucleotide sequence including coding region of ADF3 of *Araneus diadematus* added with His-tag and HRV3C protease recognition sequence at N-terminus SEQ ID NO: 5, Amino acid sequence of ADF3 of *Araneus diadematus* added with His-tag and HRV3C protease recognition sequence at N-terminus SEQ ID NO: 6, Nucleotide sequence of tryptophan promoter (trp promoter) of *Escherichia coli* K-12 MG1655 strain SEQ ID NO: 7, Nucleotide sequence of ampicillin resistance gene promoter (bla promoter)

SEQ ID NO: 8, Nucleotide sequence of tryptophan repressor gene (trpR gene) of *Escherichia coli* K-12 MG1655 strain SEQ ID NO: 9, Amino acid sequence of tryptophan repressor (TrpR) of *Escherichia coli* K-12 MG1655 strain SEQ ID NOS: 10-11, Primers SEQ ID NO: 12, attL-Km$^r$-attL sequence SEQ ID NOS: 13-19, Primers

The invention claimed is:

1. A method for producing a fibroin-like protein, the method comprising:
   (A) culturing *Escherichia coli* having a gene encoding the fibroin-like protein in a medium;
   (B) inducing expression of the gene encoding the fibroin-like protein during said culturing; and
   (C) collecting the fibroin-like protein,
   wherein when said inducing expression occurs, accumulation of an organic acid is reduced, and
   wherein the gene is expressed under the control of a tryptophan promoters;
   wherein said inducing expression occurs by depleting tryptophan in the medium, adding 3-beta-indoleacrylic acid to the medium, or a combination thereof;
   wherein the fibroin-like protein is selected from the group consisting of:
   (X) fibroin,
   (Y) a fibrous protein having a sequence similar to a repetitive sequence of fibroin, and
   (Z) combinations thereof;
   wherein the sequence similar to a repetitive sequence of fibroin is represented by formula (I),
   REP1-REP2 ... (I);
   wherein the fibrous protein having a sequence similar to a repetitive sequence of a fibroin comprises 2 or more repetitions of the sequence represented by formula (I);
   wherein, independently for each repetition, said REP1 is a continuous amino acid sequence of one or more of alanine and glycine, and the length of said REP1 is 2 to 20 residues; and
   wherein, independently for each repetition, said REP2 is a continuous amino acid sequence comprising amino acids selected from the group consisting of glycine, serine, glutamine, and alanine; wherein the total number of glycine, serine, glutamine, and alanine residues is 40% or more of the total number of amino acid residues of the REP2, and the length of the REP2 is 2 to 200 residues.

2. The method according to claim 1, wherein said inducing expression occurs either by depleting tryptophan in the medium, or by depleting tryptophan in the medium and adding 3-beta-indoleacrylic acid to the medium.

3. The method according to claim 1, wherein the concentration of tryptophan in the medium is lowerthan 50 mg/L during said depleting.

4. The method according to claim 1,
wherein the step (A) comprises a culture period A1 and a culture period A2,
wherein the culture period A2 occurs after the culture period A1,
wherein the concentration of tryptophan in the medium during the culture period A1 is 50 mg/L or higher, and
wherein the concentration tryptophan in the medium during the culture period A2 is lower than 50 mg/L.

5. The method according to claim 4, wherein said inducing expression occurs at the timepoint of switching from the culture period A1 to the culture period A2.

6. The method according to claim 1, wherein at the beginning of said culturing, the medium contains tryptophan at a concentration of 50 mg/L or higher.

7. The method according to claim 1, wherein 3-beta-indoleacrylic acid is added to the medium before said culturing but said inducing expression occurs by depleting tryptophan in the medium during said culturing.

8. The method according to claim 1, wherein said inducing expression occurs by adding 3-beta-indoleacrylic acid to the medium during said culturing.

9. The method according to claim 1, wherein the amount of organic acid that has accumulated in the medium at the time of said inducing the expression is 3.3 g/L or lower.

10. The method according to claim 1, wherein OD620 at the time of said inducing the expression is 50 or more.

11. The method according to claim 1, wherein said accumulation of the organic acid is reduced by limiting the amount of a carbon source during a period before said inducing the expression.

12. The method according to claim 11, wherein the carbon source in the medium is limited to 1.0 g/L or lower during the period before said inducing the expression.

13. The method according to claim 11, wherein the carbon source is glucose.

14. The method according to claim 1, wherein the accumulation of the organic acid is reduced by modifying the *Escherichia coli* so that an ability to produce the organic acid is reduced.

15. The method according to claim 1, wherein the *Escherichia coli* is auxotrophic for tryptophan.

\* \* \* \* \*

SEQUENCE LISTING

```
<160> NUMBER OF SEQ ID NOS: 19

<210> SEQ ID NO 1
<211> LENGTH: 3465
<212> TYPE: DNA
<213> ORGANISM: Artificial Sequence
<220> FEATURE:
<223> OTHER INFORMATION: fibroin-like protein gene
<220> FEATURE:
<221> NAME/KEY: CDS
<222> LOCATION: (1)..(3465)

<400> SEQUENCE: 1 atg cat cac cat cat cat cac cac cac cat tcc tcg ggc tca tcc        48
Met His His His His His His His His His Ser Ser Gly Ser Ser
1               5                   10                  15 ttg gaa gtg tta ttt caa gga cca gca cga gcc ggt tcg gga caa caa    96
Leu Glu Val Leu Phe Gln Gly Pro Ala Arg Ala Gly Ser Gly Gln Gln
            20                  25                  30 ggg cct ggc cag cag ggc cca ggt caa caa ggg cca gga cag cag ggt   144
Gly Pro Gly Gln Gln Gly Pro Gly Gln Gln Gly Pro Gly Gln Gln Gly
        35                  40                  45 cct tat ggg ccc ggc gca agc gca gca gct gcg gcc gct ggt ggc tat   192
Pro Tyr Gly Pro Gly Ala Ser Ala Ala Ala Ala Ala Ala Gly Gly Tyr
    50                  55                  60 ggt cct ggc tcc ggt caa cag ggc cct tcg caa caa ggt ccc ggg cag   240
Gly Pro Gly Ser Gly Gln Gln Gly Pro Ser Gln Gln Gly Pro Gly Gln
65                  70                  75                  80 caa ggt cct ggt ggc cag ggt ccc tac ggg ccg ggg gcg agt gcg gca   288
Gln Gly Pro Gly Gly Gln Gly Pro Tyr Gly Pro Gly Ala Ser Ala Ala
                85                  90                  95 gca gcc gct gca ggc ggt tat ggt cca gga agc gga cag caa ggt ccg   336
Ala Ala Ala Ala Gly Gly Tyr Gly Pro Gly Ser Gly Gln Gln Gly Pro
            100                 105                 110 gga ggt caa ggt ccg tat ggc cca ggc tct agc gcg gct gcc gct gcc   384
Gly Gly Gln Gly Pro Tyr Gly Pro Gly Ser Ser Ala Ala Ala Ala Ala
        115                 120                 125 gcg ggt ggc aac gga cca ggg agc gga caa cag ggc gcg gga caa cag   432
Ala Gly Gly Asn Gly Pro Gly Ser Gly Gln Gln Gly Ala Gly Gln Gln
    130                 135                 140 ggt cca gga cag caa ggc cca ggg gcg tcg gcg gct gca gcg gcg gcc   480
```

```
Gly Pro Gly Gln Gln Gly Pro Gly Ala Ser Ala Ala Ala Ala Ala
145                 150                 155                 160 gga ggc tat gga ccc ggc tca gga caa cag gga ccg ggt caa caa gga        528
Gly Gly Tyr Gly Pro Gly Ser Gly Gln Gln Gly Pro Gly Gln Gln Gly
            165                 170                 175 ccc ggt ggc caa ggc ccc tat ggc ccg ggc gcc agc gcg gcc gca gcc        576
Pro Gly Gly Gln Gly Pro Tyr Gly Pro Gly Ala Ser Ala Ala Ala Ala
                180                 185                 190 gcc gcg ggc ggg tac ggc ccg gtg agc ggc cag gga cca ggt cag cag        624
Ala Ala Gly Gly Tyr Gly Pro Gly Ser Gly Gln Gly Pro Gly Gln Gln
            195                 200                 205 ggg cca gga ggt cag ggc cca tac ggt ccg ggc gca tcc gcg gcg gcg        672
Gly Pro Gly Gly Gln Gly Pro Tyr Gly Pro Gly Ala Ser Ala Ala Ala
        210                 215                 220 gca gcg gca ggt ggc tac ggt ccc gga agc ggc caa cag ggg cca ggg        720
Ala Ala Ala Gly Gly Tyr Gly Pro Gly Ser Gly Gln Gln Gly Pro Gly
225                 230                 235                 240 caa caa gga cca gga caa caa ggt cct ggg ggc caa gga ccg tat gga        768
Gln Gln Gly Pro Gly Gln Gln Gly Pro Gly Gly Gln Gly Pro Tyr Gly
                245                 250                 255 cca gga gca tca gct gca gcc gcg gca gct ggc ggt tac ggt cca ggc        816
Pro Gly Ala Ser Ala Ala Ala Ala Ala Gly Gly Tyr Gly Pro Gly
            260                 265                 270 tac ggc cag cag ggt ccg ggt cag cag gga ccg gga ggc cag ggg cct        864
Tyr Gly Gln Gln Gly Pro Gly Gln Gln Gly Pro Gly Gly Gln Gly Pro
        275                 280                 285 tat ggc cct ggc gct tcc gca gcc agt gcc gct tct gga gga tac ggg        912
Tyr Gly Pro Gly Ala Ser Ala Ala Ser Ala Ala Ser Gly Gly Tyr Gly
290                 295                 300 ccg gga agc ggt cag caa ggc cct ggc caa caa gga cct gga ggc caa        960
Pro Gly Ser Gly Gln Gln Gly Pro Gly Gln Gln Gly Pro Gly Gly Gln
305                 310                 315                 320 ggg ccc tac ggc cca gga gcc tcg gca gcc gca gct gcc gca ggt ggg       1008
Gly Pro Tyr Gly Pro Gly Ala Ser Ala Ala Ala Ala Ala Gly Gly
                325                 330                 335 tat ggg cca ggt agc ggg caa caa ggg ccg ggt cag caa gga ccg ggg       1056
Tyr Gly Pro Gly Ser Gly Gln Gln Gly Pro Gly Gln Gln Gly Pro Gly
            340                 345                 350 caa cag gga cct ggg cag caa gga ccc ggg ggt caa ggc ccg tac gga       1104
Gln Gln Gly Pro Gly Gln Gln Gly Pro Gly Gly Gln Gly Pro Tyr Gly
        355                 360                 365 cct ggt gcg tct gca gct gct gct gcg gct ggt gga tat ggt ccg gga       1152
Pro Gly Ala Ser Ala Ala Ala Ala Ala Ala Gly Gly Tyr Gly Pro Gly
370                 375                 380 tcg ggg cag cag ggt ccc ggt cag cag ggc cct ggt cag caa ggg cca       1200
Ser Gly Gln Gln Gly Pro Gly Gln Gln Gly Pro Gly Gln Gln Gly Pro
385                 390                 395                 400 ggc caa cag gga ccc gga caa caa ggc ccg ggt caa cag ggt cct gga       1248
Gly Gln Gln Gly Pro Gly Gln Gln Gly Pro Gly Gln Gln Gly Pro Gly
                405                 410                 415 cag cag ggg ccg ggc caa caa ggc cct ggg caa cag ggt ccg ggg gga       1296
Gln Gln Gly Pro Gly Gln Gln Gly Pro Gly Gln Gln Gly Pro Gly Gly
            420                 425                 430 cag ggg gcc tat ggg cct ggc gca tct gcc gcc gct gcc gca gcc ggt       1344
Gln Gly Ala Tyr Gly Pro Gly Ala Ser Ala Ala Ala Ala Ala Ala Gly
        435                 440                 445 ggg tac ggg cct ggg tca ggt caa cag ggg cct ggt caa caa ggc ccc       1392
Gly Tyr Gly Pro Gly Ser Gly Gln Gln Gly Pro Gly Gln Gln Gly Pro
450                 455                 460
```

-continued

| | | |
|---|---|---|
| ggg caa cag ggc ccc ggc cag caa ggt cca ggg cag cag ggc ccg gga<br>Gly Gln Gln Gly Pro Gly Gln Gln Gly Pro Gly Gln Gln Gly Pro Gly<br>465                      470                    475                  480 | 1440 |
| cag caa ggg cct gga caa cag ggg ccc gga cag cag gga cct tac ggg<br>Gln Gln Gly Pro Gly Gln Gln Gly Pro Gly Gln Gln Gly Pro Tyr Gly<br>                    485                    490                    495 | 1488 |
| ccc ggt gcg agc gca gcg gcc gcc gca ggg gga tat ggc ccc gga<br>Pro Gly Ala Ser Ala Ala Ala Ala Ala Gly Gly Tyr Gly Pro Gly<br>500                      505                    510 | 1536 |
| tcg ggc cag cag gga cca ggc cag caa gga cct ggc caa cag ggc ccg<br>Ser Gly Gln Gln Gly Pro Gly Gln Gln Gly Pro Gly Gln Gln Gly Pro<br>                    515                    520                    525 | 1584 |
| ggg ggt cag ggg ccg tat ggt ccc ggc gct gca agt gct gca gtg tcc<br>Gly Gln Gly Pro Tyr Gly Pro Gly Ala Ala Ser Ala Ala Val Ser<br>530                      535                    540 | 1632 |
| gtt tct aga gca cga gcc ggt tcg gga caa caa ggg cct ggc cag cag<br>Val Ser Arg Ala Arg Ala Gly Ser Gly Gln Gln Gly Pro Gly Gln Gln<br>545                      550                    555                    560 | 1680 |
| ggc cca ggt caa caa ggg cca gga cag cag ggt cct tat ggg ccc ggc<br>Gly Pro Gly Gln Gln Gly Pro Gly Gln Gln Gly Pro Tyr Gly Pro Gly<br>                    565                    570                    575 | 1728 |
| gca agc gca gca gct gcg gcc gct ggt ggc tat ggt cct ggc tcc ggt<br>Ala Ser Ala Ala Ala Ala Ala Gly Gly Tyr Gly Pro Gly Ser Gly<br>              580                    585                    590 | 1776 |
| caa cag ggc cct tcg caa caa ggt ccc ggg cag caa ggt cct ggt ggc<br>Gln Gln Gly Pro Ser Gln Gln Gly Pro Gly Gln Gln Gly Pro Gly Gly<br>                    595                    600                    605 | 1824 |
| cag ggt ccc tac ggg ccg ggg gcg agt gcg gca gca gcc gct gca ggc<br>Gln Gly Pro Tyr Gly Pro Gly Ala Ser Ala Ala Ala Ala Ala Gly<br>610                      615                    620 | 1872 |
| ggt tat ggt cca gga agc gga cag caa ggt ccg gga ggt caa ggt ccg<br>Gly Tyr Gly Pro Gly Ser Gly Gln Gln Gly Pro Gly Gly Gln Gly Pro<br>625                      630                    635                    640 | 1920 |
| tat ggc cca ggc tct agc gcg gct gcc gct gcc gcg ggt ggc aac gga<br>Tyr Gly Pro Gly Ser Ser Ala Ala Ala Ala Ala Gly Gly Asn Gly<br>                    645                    650                    655 | 1968 |
| cca ggg agc gga caa cag ggc gcg gga caa cag ggt cca gga cag caa<br>Pro Gly Ser Gly Gln Gln Gly Ala Gly Gln Gln Gly Pro Gly Gln Gln<br>                    660                    665                    670 | 2016 |
| ggc cca ggg gcg tcg gcg gct gca gcg gcg gcc gga ggc tat gga ccc<br>Gly Pro Gly Ala Ser Ala Ala Ala Ala Ala Gly Gly Tyr Gly Pro<br>              675                    680                    685 | 2064 |
| ggc tca gga caa cag gga ccg ggt caa caa gga ccc ggt ggc caa ggc<br>Gly Ser Gly Gln Gln Gly Pro Gly Gln Gln Gly Pro Gly Gly Gln Gly<br>690                      695                    700 | 2112 |
| ccc tat ggc ccg ggc gcc agc gcg gcc gca gcc gcc gcg ggc ggg tac<br>Pro Tyr Gly Pro Gly Ala Ser Ala Ala Ala Ala Ala Ala Gly Gly Tyr<br>705                      710                    715                    720 | 2160 |
| ggc ccc ggt agc ggc cag gga cca ggt cag cag ggg cca gga ggt cag<br>Gly Pro Gly Ser Gly Gln Gly Pro Gly Gln Gln Gly Pro Gly Gly Gln<br>                    725                    730                    735 | 2208 |
| ggc cca tac ggt ccg ggc gca tcc gcg gcg gcg gca gcg gca ggt ggc<br>Gly Pro Tyr Gly Pro Gly Ala Ser Ala Ala Ala Ala Ala Ala Gly Gly<br>                    740                    745                    750 | 2256 |
| tac ggt ccc gga agc ggc caa cag ggg cca ggg caa caa gga cca gga<br>Tyr Gly Pro Gly Ser Gly Gln Gln Gly Pro Gly Gln Gln Gly Pro Gly<br>                    755                    760                    765 | 2304 |
| caa caa ggt cct ggg ggc caa gga ccg tat gga cca gga gca tca gct<br>Gln Gln Gly Pro Gly Gly Gln Gly Pro Tyr Gly Pro Gly Ala Ser Ala<br>770                      775                    780 | 2352 |

```
gca gcc gcg gca gct ggc ggt tac ggt cca ggc tac ggc cag cag ggt       2400
Ala Ala Ala Ala Ala Gly Gly Tyr Gly Pro Gly Tyr Gly Gln Gln Gly
785                 790                 795                 800 ccg ggt cag cag gga ccg gga ggc cag ggg cct tat ggc cct ggc gct       2448
Pro Gly Gln Gln Gly Pro Gly Gly Gln Gly Pro Tyr Gly Pro Gly Ala
                805                 810                 815 tcc gca gcc agt gcc gct tct gga gga tac ggg ccg gga agc ggt cag       2496
Ser Ala Ala Ser Ala Ala Ser Gly Gly Tyr Gly Pro Gly Ser Gly Gln
            820                 825                 830 caa ggc cct ggc caa caa gga cct gga ggc caa ggg ccc tac ggc cca       2544
Gln Gly Pro Gly Gln Gln Gly Pro Gly Gly Gln Gly Pro Tyr Gly Pro
        835                 840                 845 gga gcc tcg gca gcc gca gct gcc gca ggt ggg tat ggg cca ggt agc       2592
Gly Ala Ser Ala Ala Ala Ala Ala Gly Gly Tyr Gly Pro Gly Ser
    850                 855                 860 ggg caa caa ggg ccg ggt cag caa gga ccg ggg caa cag gga cct ggg       2640
Gly Gln Gln Gly Pro Gly Gln Gln Gly Pro Gly Gln Gln Gly Pro Gly
865                 870                 875                 880 cag caa gga ccc ggg ggt caa ggc ccg tac gga cct ggt gcg tct gca       2688
Gln Gln Gly Pro Gly Gly Gln Gly Pro Tyr Gly Pro Gly Ala Ser Ala
                885                 890                 895 gct gct gct gcg gct ggt gga tat ggt ccg gga tcg ggg cag cag ggt       2736
Ala Ala Ala Ala Ala Gly Gly Tyr Gly Pro Gly Ser Gly Gln Gln Gly
            900                 905                 910 ccc ggt cag cag ggc cct ggt cag caa ggg cca ggc caa cag gga ccc       2784
Pro Gly Gln Gln Gly Pro Gly Gln Gln Gly Pro Gly Gln Gln Gly Pro
        915                 920                 925 gga caa caa ggc ccg ggt caa cag ggt cct gga cag cag ggg ccg ggc       2832
Gly Gln Gln Gly Pro Gly Gln Gln Gly Pro Gly Gln Gln Gly Pro Gly
    930                 935                 940 caa caa ggc cct ggg caa cag ggt ccg ggg gga cag ggg gcc tat ggg       2880
Gln Gln Gly Pro Gly Gln Gln Gly Pro Gly Gly Gln Gly Ala Tyr Gly
945                 950                 955                 960 cct ggc gca tct gcc gcc gct ggc gca gcc ggt ggg tac ggg cct ggg       2928
Pro Gly Ala Ser Ala Ala Ala Gly Ala Ala Gly Gly Tyr Gly Pro Gly
                965                 970                 975 tca ggt caa cag ggg cct ggt caa caa ggc ccc ggg caa cag ggc ccc       2976
Ser Gly Gln Gln Gly Pro Gly Gln Gln Gly Pro Gly Gln Gln Gly Pro
            980                 985                 990 ggc cag caa ggt cca ggg cag cag  ggc ccg gga cag caa  ggg cct gga     3024
Gly Gln Gln Gly Pro Gly Gln Gln  Gly Pro Gly Gln Gln  Gly Pro Gly
        995                 1000                 1005 caa cag  ggg ccc gga cag cag  gga cct tac ggg ccc  ggt gcg agc        3069
Gln Gln  Gly Pro Gly Gln Gln  Gly Pro Tyr Gly Pro  Gly Ala Ser
    1010                 1015                 1020 gca gcg  gcc gcc gcc gca ggg  gga tat ggc ccc gga  tcg ggc cag        3114
Ala Ala  Ala Ala Ala Ala Gly  Gly Tyr Gly Pro Gly  Ser Gly Gln
1025                 1030                 1035 cag gga  cca ggc cag caa gga  cct ggc caa cag ggc  ccg ggg gt         3159
Gln Gly  Pro Gly Gln Gln Gly  Pro Gly Gln Gln Gly  Pro Gly Gly
    1040                 1045                 1050 cag ggg  ccg tat ggt ccc ggc  gct gca agt gct gca  gtg tcc gtt        3204
Gln Gly  Pro Tyr Gly Pro Gly  Ala Ala Ser Ala Ala  Val Ser Val
    1055                 1060                 1065 gga ggt  tac ggc cct cag tct  tcg tct gtt ccg gtg  gcg tcc gca        3249
Gly Gly  Tyr Gly Pro Gln Ser  Ser Ser Val Pro Val  Ala Ser Ala
    1070                 1075                 1080 gtt gcg  agt aga ctg tct tca  cct gct gct tca tcg  cga gta tcg        3294
Val Ala  Ser Arg Leu Ser Ser  Pro Ala Ala Ser Ser  Arg Val Ser
```

```
                    1085                    1090                    1095
agc gct gtt tcg tct ctt gtc tcg tcg ggt ccc acg aaa cat gcc           3339
Ser Ala Val Ser Ser Leu Val Ser Ser Gly Pro Thr Lys His Ala
        1100                    1105                    1110 gcc ctt tca aat acg att tca tct gta gtg tcc caa gtt agt gca           3384
Ala Leu Ser Asn Thr Ile Ser Ser Val Val Ser Gln Val Ser Ala
        1115                    1120                    1125 agt aac ccg ggg tta tcc gga tgc gac gtt ctc gtt cag gca ctc           3429
Ser Asn Pro Gly Leu Ser Gly Cys Asp Val Leu Val Gln Ala Leu
        1130                    1135                    1140 cta gaa gta gta tcc gcg ttg gtg agc atc tta taa                       3465
Leu Glu Val Val Ser Ala Leu Val Ser Ile Leu
        1145                    1150

<210> SEQ ID NO 2
<211> LENGTH: 1154
<212> TYPE: PRT
<213> ORGANISM: Artificial Sequence
<220> FEATURE:
<223> OTHER INFORMATION: Synthetic Construct

<400> SEQUENCE: 2

Met His His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270
```

```
Tyr Gly Gln Gln Gly Pro Gln Gln Gly Pro Gly Gln Gly Pro
            275                 280                 285

Tyr Gly Pro Gly Ala Ser Ala Ala Ser Ala Ala Ser Gly Gly Tyr Gly
        290                 295                 300

Pro Gly Ser Gly Gln Gln Gly Pro Gln Gln Gly Pro Gly Gln
305                 310                 315                 320

Gly Pro Tyr Gly Pro Gly Ala Ser Ala Ala Ala Ala Gly Gly
                325                 330                 335

Tyr Gly Pro Gly Ser Gly Gln Gln Gly Pro Gln Gln Gly Pro Gly
            340                 345                 350

Gln Gln Gly Pro Gly Gln Gln Gly Pro Gly Gln Gly Pro Tyr Gly
        355                 360                 365

Pro Gly Ala Ser Ala Ala Ala Ala Ala Gly Gly Tyr Gly Pro Gly
        370                 375                 380

Ser Gly Gln Gln Gly Pro Gln Gln Gly Pro Gly Gln Gln Gly Pro
385                 390                 395                 400

Gly Gln Gln Gly Pro Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
        450                 455                 460

Gly Gln Gln Gly Pro Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
        530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Gly
        610                 615                 620

Gly Tyr Gly Pro Gly Ser Gly Gln Gln Gly Pro Gly Gln Gly Pro
625                 630                 635                 640

Tyr Gly Pro Gly Ser Ser Ala Ala Ala Ala Ala Gly Gly Asn Gly
                645                 650                 655

Pro Gly Ser Gly Gln Gln Gly Ala Gln Gln Gly Pro Gln Gln
            660                 665                 670

Gly Pro Gly Ala Ser Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
```

```
                690             695             700
Pro Tyr Gly Pro Gly Ala Ser Ala Ala Ala Ala Ala Gly Tyr
705                 710             715             720

Gly Pro Gly Ser Gly Gln Gly Pro Gln Gln Gly Pro Gly Gln
                725             730             735

Gly Pro Tyr Gly Pro Gly Ala Ser Ala Ala Ala Ala Gly Gly
                740             745             750

Tyr Gly Pro Gly Ser Gly Gln Gln Gly Pro Gln Gln Gly Pro
                755             760             765

Gly Gln Gln Gly Pro Gly Gln Gly Pro Tyr Gly Pro Gly Ala Ser Ala
                770             775             780

Ala Ala Ala Ala Gly Gly Tyr Gly Pro Gly Tyr Gly Gln Gln Gly
785             790             795             800

Pro Gly Gln Gln Gly Pro Gly Gln Gly Pro Tyr Gly Pro Gly Ala
                805             810             815

Ser Ala Ala Ser Ala Ala Ser Gly Gly Tyr Gly Pro Gly Ser Gly Gln
                820             825             830

Gln Gly Pro Gly Gln Gln Gly Pro Gly Gln Gly Pro Tyr Gly Pro
                835             840             845

Gly Ala Ser Ala Ala Ala Ala Ala Gly Gly Tyr Gly Pro Gly Ser
850                 855             860

Gly Gln Gln Gly Pro Gly Gln Gln Gly Pro Gly Gln Gln Gly Pro Gly
865                 870             875             880

Gln Gln Gly Pro Gly Gly Gln Gly Pro Tyr Gly Pro Gly Ala Ser Ala
                885             890             895

Ala Ala Ala Ala Gly Gly Tyr Gly Pro Gly Ser Gly Gln Gln Gly
                900             905             910

Pro Gly Gln Gln Gly Pro Gly Gln Gln Gly Pro Gly Gln Gln Gly Pro
                915             920             925

Gly Gln Gln Gly Pro Gly Gln Gln Gly Pro Gly Gln Gln Gly Pro Gly
                930             935             940

Gln Gln Gly Pro Gly Gln Gln Gly Pro Gly Gln Gln Gly Ala Tyr Gly
945                 950             955             960

Pro Gly Ala Ser Ala Ala Ala Gly Ala Ala Gly Gly Tyr Gly Pro Gly
                965             970             975

Ser Gly Gln Gln Gly Pro Gly Gln Gln Gly Pro Gly Gln Gln Gly Pro
                980             985             990

Gly Gln Gln Gly Pro Gly Gln Gln Gly Pro Gly Gln Gln Gly Pro Gly
                995             1000            1005

Gln Gln Gly Pro Gly Gln Gln Gly Pro Tyr Gly Pro Gly Ala Ser
                1010            1015            1020

Ala Ala Ala Ala Ala Ala Gly Gly Tyr Gly Pro Gly Ser Gly Gln
1025                1030            1035

Gln Gly Pro Gly Gln Gln Gly Pro Gly Gln Gln Gly Pro Gly Gly
                1040            1045            1050

Gln Gly Pro Tyr Gly Pro Gly Ala Ala Ser Ala Ala Val Ser Val
                1055            1060            1065

Gly Gly Tyr Gly Pro Gln Ser Ser Ser Val Pro Val Ala Ser Ala
                1070            1075            1080

Val Ala Ser Arg Leu Ser Ser Pro Ala Ala Ser Ser Arg Val Ser
                1085            1090            1095

Ser Ala Val Ser Ser Leu Val Ser Ser Gly Pro Thr Lys His Ala
                1100            1105            1110
```

-continued

Ala Leu Ser Asn Thr Ile Ser Ser Val Val Ser Gln Val Ser Ala
1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 3
<211> LENGTH: 636
<212> TYPE: PRT
<213> ORGANISM: Araneus diadematus

<400> SEQUENCE: 3

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
                20                  25                  30

Ala Ala Ala Ala Ala Gly Gly Tyr Gly Pro Gly Ser Gly Gln Gln Gly
            35                  40                  45

Pro Ser Gln Gln Gly Pro Gly Gln Gln Gly Pro Gly Gln Gln Gly Pro
50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gln Gly Pro Tyr Gly Pro
                85                  90                  95

Gly Ser Ser Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
        115                 120                 125

Ala Ser Ala Ala Ala Ala Ala Gly Gly Tyr Gly Pro Gly Ser Gly
130                 135                 140

Gln Gln Gly Pro Gly Gln Gln Gly Pro Gly Gln Gln Gly Pro Tyr Gly
145                 150                 155                 160

Pro Gly Ala Ser Ala Ala Ala Ala Ala Gly Gly Tyr Gly Pro Gly
            165                 170                 175

Ser Gly Gln Gly Pro Gly Gln Gln Gly Pro Gly Gln Gln Gly Pro Tyr
                180                 185                 190

Gly Pro Gly Ala Ser Ala Ala Ala Ala Ala Gly Gly Tyr Gly Pro
            195                 200                 205

Gly Ser Gly Gln Gln Gly Pro Gly Gln Gln Gly Pro Gly Gln Gln Gly
        210                 215                 220

Pro Gly Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
        275                 280                 285

Gly Gln Gln Gly Pro Gly Gly Gly Pro Tyr Gly Pro Gly Ala Ser
        290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly

```
              325                 330                 335
Pro Gly Gly Gln Gly Pro Tyr Gly Pro Gly Ala Ser Ala Ala Ala Ala
                340                 345                 350
Ala Ala Gly Gly Tyr Gly Pro Gly Ser Gly Gln Gln Gly Pro Gly Gln
                355                 360                 365
Gln Gly Pro Gly Gln Gln Gly Pro Gly Gln Gln Gly Pro Gly Gln Gln
                370                 375                 380
Gly Pro Gly Gln Gln Gly Pro Gly Gln Gln Gly Pro Gly Gln Gln Gly
385                 390                 395                 400
Pro Gly Gln Gln Gly Pro Gly Gly Gln Gly Ala Tyr Gly Pro Gly Ala
                405                 410                 415
Ser Ala Ala Ala Gly Ala Ala Gly Gly Tyr Gly Pro Gly Ser Gly Gln
                420                 425                 430
Gln Gly Pro Gly Gln Gln Gly Pro Gly Gln Gln Gly Pro Gly Gln Gln
                435                 440                 445
Gly Pro Gly Gln Gln Gly Pro Gly Gln Gln Gly Pro Gly Gln Gln Gly
                450                 455                 460
Pro Gly Gln Gln Gly Pro Tyr Gly Pro Gly Ala Ser Ala Ala Ala Ala
465                 470                 475                 480
Ala Ala Gly Gly Tyr Gly Pro Gly Ser Gly Gln Gln Gly Pro Gly Gln
                485                 490                 495
Gln Gly Pro Gly Gln Gln Gly Pro Gly Gly Gln Gly Pro Tyr Gly Pro
                500                 505                 510
Gly Ala Ala Ser Ala Ala Val Ser Val Gly Gly Tyr Gly Pro Gln Ser
                515                 520                 525
Ser Ser Val Pro Val Ala Ser Ala Val Ala Ser Arg Leu Ser Ser Pro
                530                 535                 540
Ala Ala Ser Ser Arg Val Ser Ser Ala Val Ser Ser Leu Val Ser Ser
545                 550                 555                 560
Gly Pro Thr Lys His Ala Ala Leu Ser Asn Thr Ile Ser Ser Val Val
                565                 570                 575
Ser Gln Val Ser Ala Ser Asn Pro Gly Leu Ser Gly Cys Asp Val Leu
                580                 585                 590
Val Gln Ala Leu Leu Glu Val Val Ser Ala Leu Val Ser Ile Leu Gly
                595                 600                 605
Ser Ser Ser Ile Gly Gln Ile Asn Tyr Gly Ala Ser Ala Gln Tyr Thr
                610                 615                 620
Gln Met Val Gly Gln Ser Val Ala Gln Ala Leu Ala
625                 630                 635

<210> SEQ ID NO 4
<211> LENGTH: 2190
<212> TYPE: DNA
<213> ORGANISM: Araneus diadematus

<400> SEQUENCE: 4
agatatacat aatgcaccac catcaccacc atcatcacca tcatagcagc ggcagcagcc      60
tggaagttct gtttcagggt ccggcgcgtg cgggtagcgg ccagcagggc ccgggtcagc     120
agggtccggg ccaacaaggt ccgggccagc agggcccgta tggtccgggt gcaagcgcag     180
cagcagcggc cgcaggcggt tacggcccgg gtagcggcca gcagggcccg agccagcagg     240
gcccgggcca gcagggtccg gcggtcaggg tccgtacgg tccggcgcg agcgcggccg     300 ccgcggccgc aggcggttac gggccgggca gcggtcagca gggcccgggc ggtcagggcc     360
```

-continued

| | |
|---|---|
| cgtatggccc gggtagcagc gcggccgcgg cggccgcagg cggtaatggt ccgggcagcg | 420 |
| gccagcaggg tgcgggccaa caaggcccgg gtcagcaggg cccgggtgcc agcgccgccg | 480 |
| cagcggccgc aggcggttac ggtccgggta gcggtcagca gggtcctggc aacaaggcc | 540 |
| cgggcggtca aggtccttac ggcccgggcg ccagcgccgc ggctgcggcc gcaggcggtt | 600 |
| acggaccggg tagcggccag ggtcctggtc aacaaggtcc gggcggtcaa ggcccgtatg | 660 |
| gtccgggcgc cagcgcggcg gccgcggccg caggcggtta cgggccaggt agcggccagc | 720 |
| agggtcctgg ccagcagggt cctggacaac aaggaccggg cggtcaagga ccgtacggcc | 780 |
| cgggcgcgag cgccgcggca gcggccgcag gcggttatgg tccgggttac ggtcagcagg | 840 |
| gtcccggtca acagggaccg ggcggtcaag gtccgtatgg cccgggtgcg agcgcggcca | 900 |
| gcgcagcgag cggcggttac ggtcctggtt ctggtcagca gggtcctgga cagcaaggtc | 960 |
| cgggcggtca gggaccttac ggtccgggtg cgagcgccgc agcggccgca gcgggcggtt | 1020 |
| acggccctgg ctctggtcag cagggtccag gtcaacaggg tcctggtcaa cagggtcccg | 1080 |
| gtcagcaagg cccgggcggt cagggtcctt atggtccggg cgcaagcgcg ccgccgccg | 1140 |
| cagcgggcgg ttacggtcct ggcagtggtc agcagggtcc gggacaacag gtcctggac | 1200 |
| agcagggtcc tgggcagcag ggtcctggtc agcaaggtcc tggtcagcag ggccctggcc | 1260 |
| agcagggtcc cggtcagcag ggccctggtc aacaaggacc gggcggtcag ggcgcgtatg | 1320 |
| gtccgggtgc cagcgccgca gcgggcgccg caggcggtta cgggcctggt agtggtcaac | 1380 |
| aggggcctgg ccaacagggc cctggtcagc aaggccctgg tcaacagggc cctggtcagc | 1440 |
| agggccccgg tcaacagggc cccggtcaac agggtccagg tcagcaaggt ccgtacggcc | 1500 |
| cgggcgcaag cgccgcggca gcggccgcag gcggttacgg gcccggctct ggtcaacagg | 1560 |
| ggcccggtca acagggccca ggtcaacagg ggccgggcgg tcaagggcct tatgccccgg | 1620 |
| gcgccgcgag cgccgccgtg agcgttggcg gttacggtcc gcagagcagc agcgtgccgg | 1680 |
| ttgccagcgc agtggccagc cgcctgagca gcccggccgc gagcagccgt gtgagcagcg | 1740 |
| cagttagcag cttagtgagc agcggtccga ccaaacatgc cgcgctgagc aacacgatta | 1800 |
| gcagcgtggt tagccaggtt tctgcaagca atccgggtct gagcggttgc gatgtgctgg | 1860 |
| ttcaggcgct gctggaagtg gttagcgcct tagtgagcat cctgggcagc agcagcattg | 1920 |
| gccagatcaa ttatggcgcg agcgcccagt acacccagat ggttggtcag agcgtggcac | 1980 |
| aggccctggc gtgaaattcg agctccgtcg acaagcttgc ggccgcactc gagcaccacc | 2040 |
| accaccacca ctgagatccg gctgctaaca aagcccgaaa ggaagctgag ttggctgctg | 2100 |
| ccaccgctga gcaataacta gcataacccc ttggggcctc taaacgggtc ttgagggt | 2160 |
| ttttgctgaa aggaggaact atatccggat | 2190 |

<210> SEQ ID NO 5
<211> LENGTH: 660
<212> TYPE: PRT
<213> ORGANISM: Araneus diadematus

<400> SEQUENCE: 5

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

-continued

```
Pro Tyr Gly Pro Gly Ala Ser Ala Ala Ala Ala Ala Gly Gly Tyr
     50                  55                  60

Gly Pro Gly Ser Gly Gln Gln Gly Pro Ser Gln Gln Gly Pro Gly Gln
 65                  70                  75                  80

Gln Gly Pro Gly Gly Gln Gly Pro Tyr Gly Pro Gly Ala Ser Ala Ala
                 85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gly Pro Tyr Gly
        355                 360                 365

Pro Gly Ala Ser Ala Ala Ala Ala Ala Ala Gly Gly Tyr Gly Pro Gly
    370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
        435                 440                 445

Gly Tyr Gly Pro Gly Ser Gly Gln Gln Gly Pro Gly Gln Gln Gly Pro
450                 455                 460

Gly Gln Gln Gly Pro Gly Gln Gln Gly Pro Gly Gln Gln Gly Pro Gly
```

-continued

```
            465                 470                 475                 480
       Gln Gln Gly Pro Gly Gln Gln Gly Pro Gly Gln Gln Gly Pro Tyr Gly
                        485                 490                 495

Pro Gly Ala Ser Ala Ala Ala Ala Ala Gly Gly Tyr Gly Pro Gly
                    500                 505                 510

Ser Gly Gln Gln Gly Pro Gly Gln Gly Pro Gly Gln Gln Gly Pro
                    515                 520                 525

Gly Gly Gln Gly Pro Tyr Gly Pro Gly Ala Ala Ser Ala Ala Val Ser
            530                 535                 540

Val Gly Gly Tyr Gly Pro Gln Ser Ser Ser Val Pro Val Ala Ser Ala
       545                 550                 555                 560

Val Ala Ser Arg Leu Ser Ser Pro Ala Ala Ser Ser Arg Val Ser Ser
                        565                 570                 575

Ala Val Ser Ser Leu Val Ser Ser Gly Pro Thr Lys His Ala Ala Leu
                    580                 585                 590

Ser Asn Thr Ile Ser Ser Val Val Ser Gln Val Ser Ala Ser Asn Pro
                    595                 600                 605

Gly Leu Ser Gly Cys Asp Val Leu Val Gln Ala Leu Leu Glu Val Val
                    610                 615                 620

Ser Ala Leu Val Ser Ile Leu Gly Ser Ser Ser Ile Gly Gln Ile Asn
       625                 630                 635                 640

Tyr Gly Ala Ser Ala Gln Tyr Thr Gln Met Val Gly Gln Ser Val Ala
                        645                 650                 655

Gln Ala Leu Ala
                    660

<210> SEQ ID NO 6
<211> LENGTH: 65
<212> TYPE: DNA
<213> ORGANISM: Escherichia coli

<400> SEQUENCE: 6
ctgttgacaa ttaatcatcg aactagttaa ctagtacgca agttcacgta aaagggtat      60 cgaca                                                                 65

<210> SEQ ID NO 7
<211> LENGTH: 132
<212> TYPE: DNA
<213> ORGANISM: Escherichia coli

<400> SEQUENCE: 7
tcaggtggca ctttcggggg aaatgtgcgc ggaaccccta tttgtttatt tttctaaata    60
cattcaaata tgtatccgct catgagacaa taaccctgat aaatgcttca ataatattga   120
aaaaggaaga gt                                                        132

<210> SEQ ID NO 8
<211> LENGTH: 327
<212> TYPE: DNA
<213> ORGANISM: Escherichia coli

<400> SEQUENCE: 8
atggcccaac aatcacccta ttcagcagcg atggcagaac agcgtcacca ggagtggtta    60
cgttttgtcg acctgcttaa gaatgcctac caaaacgatc tccatttacc gttgttaaac   120
ctgatgctga cgccagatga gcgcgaagcg ttggggactc gcgtgcgtat tgtcgaagag   180
ctgttgcgcg gcgaaatgag ccagcgtgag ttaaaaaatg aactcggcgc aggcatcgcg   240
```

```
acgattacgc gtggatctaa cagcctgaaa gccgcgcccg tcgagctgcg ccagtggctg     300
gaagaggtgt tgctgaaaag cgattga                                         327

<210> SEQ ID NO 9
<211> LENGTH: 108
<212> TYPE: PRT
<213> ORGANISM: Escherichia coli

<400> SEQUENCE: 9

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20                  25                  30

Asp Leu His Leu Pro Leu Leu Asn Leu Met Leu Thr Pro Asp Glu Arg
        35                  40                  45

Glu Ala Leu Gly Thr Arg Val Arg Ile Val Glu Glu Leu Leu Arg Gly
    50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp
            100                 105

<210> SEQ ID NO 10
<211> LENGTH: 58
<212> TYPE: DNA
<213> ORGANISM: Artificial Sequence
<220> FEATURE:
<223> OTHER INFORMATION: primer

<400> SEQUENCE: 10
aatgagcggg cttttttttg aacaaaatta gagaataaca tgaagcctgc tttttat       58

<210> SEQ ID NO 11
<211> LENGTH: 58
<212> TYPE: DNA
<213> ORGANISM: Artificial Sequence
<220> FEATURE:
<223> OTHER INFORMATION: primer

<400> SEQUENCE: 11
gaaagttaaa atgccgccag cggaactggc ggctgtggga cgctcaagtt agtataaa      58

<210> SEQ ID NO 12
<211> LENGTH: 1551
<212> TYPE: DNA
<213> ORGANISM: Artificial Sequence
<220> FEATURE:
<223> OTHER INFORMATION: attL-Kmr-attL sequence

<400> SEQUENCE: 12
ctagacgctc aagttagtat aaaaaagctg aacgagaaac gtaaaatgat ataaatatca     60
atatattaaa ttagattttg cataaaaaac agactacata atactgtaaa acacaacata    120
tgcagtcact atgaatcaac tacttagatg gtattagtga cctgtaacag actgcagggg    180 gggggggaa agccacgttg tgtctcaaaa tctctgatgt tacattgcac aagataaaaa    240
tatatcatca tgaacaataa aactgtctgc ttacataaac agtaatacaa ggggtgttat    300
gagccatatt caacgggaaa cgtcttgctc gaggccgcga ttaaattcca acatggatgc    360
```

```
tgatttatat gggtataaat gggctcgcga taatgtcggg caatcaggtg cgacaatcta    420
tcgattgtat gggaagcccg atgcgccaga gttgtttctg aaacatggca aaggtagcgt    480
tgccaatgat gttacagatg agatggtcag actaaactgg ctgacggaat ttatgcctct    540
tccgaccatc aagcatttta tccgtactcc tgatgatgca tggttactca ccactgcgat    600
ccccgggaaa acagcattcc aggtattaga agaatatcct gattcaggtg aaaatattgt    660
tgatgcgctg gcagtgttcc tgcgccggtt gcattcgatt cctgtttgta attgtccttt    720
taacagcgat cgcgtatttc gtctcgctca ggcgcaatca cgaatgaata acggtttggt    780
tgatgcgagt gattttgatg acgagcgtaa tggctggcct gttgaacaag tctggaaaga    840
aatgcataag cttttgccat tctcaccgga ttcagtcgtc actcatggtg atttctcact    900
tgataacctt attttgacg agggaaatt aataggttgt attgatgttg acgagtcgg     960 aatcgcagac cgataccagg atcttgccat cctatggaac tgcctcggtg agttttctcc   1020
ttcattacag aaacggcttt ttcaaaaata tggtattgat aatcctgata tgaataaatt   1080
gcagtttcat ttgatgctcg atgagttttt ctaatcagaa ttggttaatt ggttgtaaca   1140
ctggcagagc attacgctga cttgacggga cggcggcttt gttgaataaa tcgaactttt   1200
gctgagttga aggatcagat cacgcatctt cccgacaacg cagaccgttc cgtggcaaag   1260
caaaagttca aaatcaccaa ctggtccacc tacaacaaag ctctcatcaa ccgtggctcc   1320
ctcactttct ggctggatga tggggcgatt caggcctggt atgagtcagc aacaccttct   1380
tcacgaggca gacctcagcg ccccccccc  ctgcaggtcg acggatccgg ggaattcgaa   1440
atcaaataat gattttattt tgactgatag tgacctgttc gttgcaacaa attgataagc   1500
aatgcttttt tataatgcca acttagtata aaaaagcagg cttcaagatc t            1551

<210> SEQ ID NO 13
<211> LENGTH: 54
<212> TYPE: DNA
<213> ORGANISM: Artificial Sequence
<220> FEATURE:
<223> OTHER INFORMATION: primer

<400> SEQUENCE: 13
tagaggatcg agatcctgtt gacaattaat catcgaacta gttaactagt acgc          54

<210> SEQ ID NO 14
<211> LENGTH: 62
<212> TYPE: DNA
<213> ORGANISM: Artificial Sequence
<220> FEATURE:
<223> OTHER INFORMATION: primer

<400> SEQUENCE: 14
tgatggtgat gcatatgtcg ataccctttt tacgtgaact tgcgtactag ttaactagtt    60
cg                                                                  62

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
aatattgaaa aaggaagagt atggcccaac aatcaccecta ttcagcagcg               50
```

```
<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
taagtgcggc gacgaatcat gcctaccaaa catattgaaa ttacg              45

<210> SEQ ID NO 17
<211> LENGTH: 80
<212> TYPE: DNA
<213> ORGANISM: Artificial Sequence
<220> FEATURE:
<223> OTHER INFORMATION: primer

<400> SEQUENCE: 17
aatacattca aatatgtatc cgctcatgag acaataaccc tgataaatgc ttcaataata    60
ttgaaaaagg aagagtatgg                                                80

<210> SEQ ID NO 18
<211> LENGTH: 80
<212> TYPE: DNA
<213> ORGANISM: Artificial Sequence
<220> FEATURE:
<223> OTHER INFORMATION: primer

<400> SEQUENCE: 18
gtcaggtggc acttttcggg gaaatgtgcg cggaacccct atttgtttat ttttctaaat    60
acattcaaat atgtatccgc                                                80

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
ggcgccatct ccttgtcagg tggcactttt cggggaaatg tgc                43
```